United States Patent
Chan et al.

(10) Patent No.: US 10,675,014 B2
(45) Date of Patent: Jun. 9, 2020

(54) KNOTLESS SOFT TISSUE ATTACHMENT

(71) Applicant: Crossroads Extremity Systems, LLC, Memphis, TN (US)

(72) Inventors: Kwan-Ho Chan, Singapore (SG); James Murphy, Newton Square, PA (US); T. Wade Fallin, Hyde Park, UT (US); Patrick M. White, West Chester, PA (US)

(73) Assignee: Crossroads Extremity Systems, LLC, Memphis, TN (US)

( * ) Notice: Subject to any disclaimer, the term of this patent is extended or adjusted under 35 U.S.C. 154(b) by 0 days.

(21) Appl. No.: 15/093,577

(22) Filed: Apr. 7, 2016

(65) Prior Publication Data

US 2016/0213370 A1     Jul. 28, 2016

Related U.S. Application Data

(63) Continuation of application No. 13/674,837, filed on Nov. 12, 2012, now Pat. No. 10,136,883.
(Continued)

(51) Int. Cl.
*A61B 17/04* (2006.01)
*A61F 2/08* (2006.01)

(52) U.S. Cl.
CPC ........ *A61B 17/0401* (2013.01); *A61F 2/0811* (2013.01); *A61B 2017/0403* (2013.01);
(Continued)

(58) Field of Classification Search
CPC ........ A61B 17/0401; A61B 2017/0414; A61B 2017/0459; A61B 2017/0451; A61B 2017/0403; A61B 2017/0462; A61B 2017/0464; A61B 2017/0412; A61B 2017/0445; A61B 2017/044; A61F 2/0811; A61F 2002/0888; A61F 2002/0864; A61F 2002/0858; A61F 2002/0829

See application file for complete search history.

(56) References Cited

U.S. PATENT DOCUMENTS

| 1,583,271 A | 5/1926 | Biro |
| 1,856,721 A | 5/1932 | Nagelmann |

(Continued)

FOREIGN PATENT DOCUMENTS

| EP | 2070481 | 6/2009 |
| WO | 2010/132310 | 11/2010 |

(Continued)

OTHER PUBLICATIONS

"Arthrex PassPort Button Cannula" 6pages, (2011) Arthrex, Inc., www.arthrex.com.
(Continued)

*Primary Examiner* — Erich G Herbermann
(74) *Attorney, Agent, or Firm* — David Meibos; Maywood IP Law

(57) ABSTRACT

Devices and methods to attach soft tissue to bone include, for example, forming a transosseous bone tunnel, and forming a suture construct securing soft tissue to the bone wherein the suture construct extends from the soft tissue to the first opening, through the first opening, through the bone tunnel, through the second opening, and outside of the bone tunnel to the soft tissue.

20 Claims, 13 Drawing Sheets

Related U.S. Application Data

(60) Provisional application No. 61/560,694, filed on Nov. 16, 2011, provisional application No. 61/597,138, filed on Feb. 9, 2012.

(52) U.S. Cl.
CPC .. *A61B 2017/044* (2013.01); *A61B 2017/0412* (2013.01); *A61B 2017/0414* (2013.01); *A61B 2017/0445* (2013.01); *A61B 2017/0451* (2013.01); *A61B 2017/0459* (2013.01); *A61B 2017/0462* (2013.01); *A61B 2017/0464* (2013.01); *A61F 2002/0829* (2013.01); *A61F 2002/0858* (2013.01); *A61F 2002/0864* (2013.01); *A61F 2002/0888* (2013.01)

(56) References Cited

U.S. PATENT DOCUMENTS

| | | |
|---|---|---|
| 4,441,497 A | 4/1984 | Paudler |
| 4,622,960 A | 11/1986 | Tam |
| 4,672,957 A | 11/1987 | Hourahane |
| 4,890,615 A | 1/1990 | Caspari et al. |
| 4,898,156 A | 2/1990 | Gattuma |
| 5,152,790 A | 10/1992 | Rosenberg et al. |
| 5,176,682 A | 1/1993 | Chow |
| 5,250,055 A | 10/1993 | Moore et al. |
| 5,254,126 A | 10/1993 | Filipi et al. |
| 5,342,369 A | 8/1994 | Harryman, II |
| 5,350,380 A | 9/1994 | Goble et al. |
| 5,354,300 A | 10/1994 | Goble et al. |
| 5,417,701 A | 5/1995 | Holmes |
| 5,439,467 A | 8/1995 | Benderev et al. |
| 5,454,823 A | 10/1995 | Richardson et al. |
| 5,464,427 A | 11/1995 | Curtis |
| 5,480,403 A | 1/1996 | Lee |
| 5,486,197 A | 1/1996 | Le |
| 5,544,664 A | 8/1996 | Benderev et al. |
| 5,545,180 A | 8/1996 | Le |
| 5,562,683 A | 10/1996 | Chan |
| 5,562,687 A | 10/1996 | Chan |
| 5,569,306 A | 10/1996 | Thal |
| 5,572,770 A | 11/1996 | Boden |
| 5,575,801 A | 11/1996 | Habermeyer et al. |
| 5,584,839 A | 12/1996 | Gieringer |
| 5,601,562 A | 2/1997 | Wolf et al. |
| 5,624,446 A | 4/1997 | Harryman, II |
| 5,649,963 A | 7/1997 | McDevitt |
| 5,681,333 A | 10/1997 | Burkhart et al. |
| 5,683,419 A | 11/1997 | Thal |
| 5,688,284 A | 11/1997 | Chervitz et al. |
| 5,700,266 A | 12/1997 | Harryman, II |
| 5,702,397 A | 12/1997 | Goble et al. |
| 5,709,708 A | 1/1998 | Thal |
| 5,730,747 A | 3/1998 | Ek et al. |
| 5,746,754 A | 5/1998 | Chan |
| 5,755,728 A | 5/1998 | Maki |
| 5,776,151 A | 7/1998 | Chan |
| 5,800,447 A | 9/1998 | Wenstrom, Jr. |
| 5,824,009 A | 10/1998 | Fukuda et al. |
| 5,868,762 A | 2/1999 | Cragg et al. |
| 5,891,150 A | 4/1999 | Chan |
| 5,891,168 A | 4/1999 | Thal |
| 5,895,425 A | 4/1999 | Grafton et al. |
| 5,899,921 A | 5/1999 | Caspari et al. |
| 5,906,624 A | 5/1999 | Wenstrom, Jr. |
| 5,935,129 A | 8/1999 | McDevitt |
| 5,947,982 A | 9/1999 | Duran |
| 5,948,000 A | 9/1999 | Larsen |
| 5,964,783 A | 10/1999 | Grafton et al. |
| 6,024,758 A | 2/2000 | Thal |
| 6,045,574 A | 4/2000 | Thal |
| 6,053,916 A | 4/2000 | Moore |
| 6,099,538 A | 8/2000 | Moses et al. |
| 6,120,511 A | 9/2000 | Chan |
| 6,143,017 A | 11/2000 | Thal |
| 6,156,039 A | 12/2000 | Thal |
| 6,183,479 B1 | 2/2001 | Tormala |
| 6,290,711 B1 | 8/2001 | Caspari |
| 6,368,335 B1 | 4/2002 | Chan |
| 6,387,129 B2 | 5/2002 | Rieser et al. |
| 6,475,230 B1 * | 11/2002 | Bonutti ............. A61B 17/0487 606/232 |
| 6,511,487 B1 | 1/2003 | Oren et al. |
| 6,514,274 B1 | 2/2003 | Boucher |
| 6,517,542 B1 | 2/2003 | Papay et al. |
| 6,524,317 B1 | 2/2003 | Ritchart et al. |
| 6,527,795 B1 | 3/2003 | Lizardi |
| 6,544,281 B2 | 4/2003 | Elatrrache et al. |
| 6,599,295 B1 | 7/2003 | Tornier |
| 6,623,524 B2 | 9/2003 | Schmieding |
| 6,629,984 B1 | 10/2003 | Chan |
| 6,638,283 B2 | 10/2003 | Thal |
| 6,641,597 B2 | 11/2003 | Burkhart et al. |
| 6,652,561 B1 | 11/2003 | Tran |
| 6,656,183 B2 | 12/2003 | Colleran et al. |
| 6,666,877 B2 | 12/2003 | Morgan et al. |
| 6,692,516 B2 | 2/2004 | West, Jr. et al. |
| 6,723,107 B1 | 4/2004 | Skiba et al. |
| 6,743,233 B1 | 6/2004 | Baldwin et al. |
| 6,770,076 B2 | 8/2004 | Foerster |
| 6,855,157 B2 | 2/2005 | Foerster |
| 6,932,826 B2 | 8/2005 | Chan |
| 6,955,678 B2 | 10/2005 | Gabriel et al. |
| 6,958,067 B2 | 10/2005 | Whittaker et al. |
| 6,984,237 B2 | 1/2006 | Hatch et al. |
| 6,986,781 B2 | 1/2006 | Smith |
| 6,991,636 B2 | 1/2006 | Rose |
| 6,994,725 B1 | 2/2006 | Goble |
| 7,033,364 B1 | 4/2006 | Walters et al. |
| 7,063,724 B2 | 6/2006 | Re et al. |
| 7,077,863 B2 | 7/2006 | Schmieding et al. |
| 7,108,700 B2 | 9/2006 | Chan |
| 7,112,208 B2 | 9/2006 | Morris et al. |
| 7,175,632 B2 | 2/2007 | Singhatat et al. |
| 7,201,756 B2 | 4/2007 | Ross et al. |
| 7,247,164 B1 | 7/2007 | Ritchart et al. |
| 7,309,337 B2 | 12/2007 | Colleran et al. |
| 7,329,272 B2 | 2/2008 | Burkhart et al. |
| 7,341,592 B1 | 3/2008 | Walters et al. |
| 7,377,926 B2 | 5/2008 | Topper et al. |
| 7,381,212 B2 | 6/2008 | Topper et al. |
| 7,399,302 B2 | 7/2008 | Goble et al. |
| 7,465,308 B2 | 12/2008 | Sikora et al. |
| 7,517,357 B2 | 4/2009 | Abrams |
| 7,527,648 B2 | 5/2009 | May |
| 7,530,999 B2 | 5/2009 | Clark et al. |
| 7,569,059 B2 | 8/2009 | Cerundolo |
| 7,585,305 B2 | 9/2009 | Dreyfuss |
| 7,585,311 B2 | 9/2009 | Green et al. |
| 7,594,917 B2 | 9/2009 | Whittaker et al. |
| 7,608,084 B2 | 10/2009 | Oren et al. |
| 7,625,386 B2 | 12/2009 | Abe et al. |
| 7,655,011 B2 | 2/2010 | Whittaker et al. |
| 7,713,286 B2 | 5/2010 | Singhatat |
| 7,749,237 B2 | 7/2010 | Chan |
| 7,771,441 B2 | 8/2010 | Cerundolo |
| 7,803,173 B2 | 9/2010 | Burkhart et al. |
| 7,833,230 B2 | 11/2010 | Cerundolo |
| 7,833,244 B2 | 11/2010 | Cerundolo |
| 7,837,710 B2 | 11/2010 | Lombardo et al. |
| 7,867,251 B2 | 1/2011 | Colleran et al. |
| 7,875,058 B2 | 1/2011 | Holmes, Jr. |
| 7,879,046 B2 | 2/2011 | Weinert et al. |
| 7,879,048 B2 | 2/2011 | Bain et al. |
| 7,883,519 B2 | 2/2011 | Oren et al. |
| 7,887,564 B2 | 2/2011 | Boehringer et al. |
| 7,931,657 B2 | 4/2011 | Walters et al. |
| 7,938,847 B2 | 5/2011 | Fanton et al. |
| 7,942,914 B2 | 5/2011 | Cerundolo |
| 7,955,341 B2 | 6/2011 | Cerundolo |
| 7,963,972 B2 | 6/2011 | Foerster et al. |
| 7,976,565 B1 | 7/2011 | Meridew |
| 7,981,140 B2 | 7/2011 | Burkhart et al. |

(56) References Cited

U.S. PATENT DOCUMENTS

| | | |
|---|---|---|
| 7,988,697 B2 | 8/2011 | Miller et al. |
| 7,993,369 B2 | 8/2011 | Dreyfuss |
| 8,038,652 B2 | 10/2011 | Morrison et al. |
| 8,043,308 B2 | 10/2011 | Bittenson |
| 8,062,295 B2 | 11/2011 | McDevitt |
| 8,100,942 B1 | 1/2012 | Green et al. |
| 8,105,343 B2 | 1/2012 | White et al. |
| 8,109,966 B2 | 2/2012 | Ritchart et al. |
| 8,109,969 B1 | 2/2012 | Green et al. |
| 8,137,360 B2 | 3/2012 | Whittaker et al. |
| 8,137,381 B2 | 3/2012 | Foerster |
| 8,147,505 B2 | 4/2012 | Delli-Santi |
| 8,177,796 B2 | 5/2012 | Akyuz et al. |
| 8,202,295 B2 | 6/2012 | Kaplan |
| 8,202,297 B2 | 6/2012 | Burkhart |
| 8,231,653 B2 | 7/2012 | Dreyfuss |
| 8,262,675 B2 | 9/2012 | Cropper |
| 8,267,964 B2 | 9/2012 | Green et al. |
| 8,282,643 B2 | 10/2012 | Dross |
| 8,317,829 B2 | 11/2012 | Foerster |
| 8,317,862 B2 | 11/2012 | Troger |
| 8,409,225 B2 | 4/2013 | Bull |
| 8,444,674 B2 | 5/2013 | Kaplan |
| 8,491,595 B2 | 7/2013 | Volpi |
| 8,506,596 B2 | 8/2013 | Stone |
| 8,518,091 B2 | 8/2013 | McDevitt |
| 8,540,737 B2 | 9/2013 | Chudik |
| 8,597,328 B2 | 12/2013 | Cauldwell |
| 8,663,280 B2 | 3/2014 | Kaplan |
| 8,740,913 B2 | 6/2014 | Schneider |
| 8,747,469 B2 | 6/2014 | Wang |
| 8,790,370 B2 | 7/2014 | Spenciner |
| 8,808,326 B2 | 8/2014 | Gagliano |
| 8,961,576 B2 | 2/2015 | Hodge |
| 8,986,347 B2 | 3/2015 | Housman |
| 9,011,466 B2 | 4/2015 | Adams et al. |
| 9,023,083 B2 | 5/2015 | Foerster |
| 9,034,014 B2 | 5/2015 | Catania |
| 9,149,268 B2 | 10/2015 | Graul |
| 9,492,155 B2 * | 11/2016 | Lo ................. A61B 17/0401 |
| 2001/0016747 A1 | 8/2001 | Romano et al. |
| 2001/0037119 A1 | 11/2001 | Schmieding |
| 2001/0049529 A1 | 12/2001 | Cachia et al. |
| 2001/0049536 A1 | 12/2001 | Chan et al. |
| 2002/0111653 A1 | 8/2002 | Foerster |
| 2002/0147456 A1 | 10/2002 | Diduch et al. |
| 2002/0165546 A1 | 11/2002 | Goble et al. |
| 2003/0195528 A1 | 10/2003 | Ritchart |
| 2003/0195563 A1 | 10/2003 | Foerster |
| 2003/0229362 A1 | 12/2003 | Chan et al. |
| 2004/0098051 A1 | 5/2004 | Fallin |
| 2004/0116843 A1 | 6/2004 | Chan |
| 2004/0133239 A1 | 7/2004 | Singhatat |
| 2004/0172062 A1 | 9/2004 | Burkhart |
| 2004/0193172 A1 | 9/2004 | Ross et al. |
| 2004/0193187 A1 | 9/2004 | Boehringer et al. |
| 2004/0267317 A1 | 12/2004 | Higgins |
| 2005/0055052 A1 | 3/2005 | Lombardo et al. |
| 2005/0075668 A1 | 4/2005 | Lizardi |
| 2005/0245932 A1 | 11/2005 | Fanton et al. |
| 2005/0277986 A1 | 12/2005 | Foerster et al. |
| 2005/0283156 A1 | 12/2005 | Schmieding et al. |
| 2006/0004410 A1 | 1/2006 | Nobis et al. |
| 2006/0074438 A1 | 4/2006 | Chan |
| 2006/0079904 A1 | 4/2006 | Thal |
| 2006/0106422 A1 | 5/2006 | Del Rio et al. |
| 2006/0149258 A1 | 7/2006 | Sousa |
| 2006/0235413 A1 | 10/2006 | Denham et al. |
| 2006/0241657 A1 * | 10/2006 | Cerundolo ......... A61B 17/0401 606/148 |
| 2006/0241658 A1 | 10/2006 | Cerundolo |
| 2006/0247642 A1 | 11/2006 | Stone et al. |
| 2006/0276841 A1 | 12/2006 | Barbieri et al. |
| 2007/0088362 A1 | 4/2007 | Bonutti |
| 2007/0112352 A1 | 5/2007 | Sorensen et al. |
| 2007/0123887 A1 | 5/2007 | Hirt et al. |
| 2007/0173865 A1 | 7/2007 | Oren et al. |
| 2007/0179510 A1 | 8/2007 | Stone |
| 2007/0191849 A1 | 8/2007 | Elatrrache et al. |
| 2007/0203498 A1 | 8/2007 | Gerber et al. |
| 2007/0219558 A1 | 9/2007 | Deutsch |
| 2007/0260259 A1 | 11/2007 | Fanton et al. |
| 2007/0270854 A1 | 11/2007 | Li et al. |
| 2008/0004659 A1 | 1/2008 | Burkhart et al. |
| 2008/0009904 A1 | 1/2008 | Bourque et al. |
| 2008/0033486 A1 | 2/2008 | Whittaaker et al. |
| 2008/0077161 A1 * | 3/2008 | Kaplan .............. A61B 17/0401 606/139 |
| 2008/0215815 A1 | 5/2008 | Heaven |
| 2008/0154314 A1 | 6/2008 | McDevitt |
| 2008/0208253 A1 | 8/2008 | Dreyfuss et al. |
| 2008/0262544 A1 | 10/2008 | Burkhart et al. |
| 2008/0275453 A1 | 11/2008 | LaFosse et al. |
| 2008/0275469 A1 * | 11/2008 | Fanton ............... A61B 17/0401 606/139 |
| 2008/0278992 A1 | 11/2008 | Tarnier |
| 2008/0300629 A1 | 12/2008 | Surti |
| 2009/0018581 A1 | 1/2009 | Anderson |
| 2009/0036905 A1 | 2/2009 | Schmieding |
| 2009/0062881 A1 | 3/2009 | Burkhart et al. |
| 2009/0076544 A1 | 3/2009 | Dimatteo |
| 2009/0088708 A1 | 4/2009 | Boehringer et al. |
| 2009/0099598 A1 | 4/2009 | McDevitt |
| 2009/0112270 A1 * | 4/2009 | Lunn ................. A61B 17/0401 606/301 |
| 2009/0157124 A1 * | 6/2009 | Ferragamo ......... A61B 17/0401 606/301 |
| 2009/0187216 A1 | 7/2009 | Schmieding et al. |
| 2009/0192546 A1 | 7/2009 | Schmieding et al. |
| 2009/0218959 A1 | 9/2009 | Burkhart et al. |
| 2009/0234387 A1 | 9/2009 | Miller et al. |
| 2009/0292313 A1 | 11/2009 | Anspach, III |
| 2009/0292321 A1 | 11/2009 | Collette |
| 2009/0312794 A1 | 12/2009 | Nason |
| 2009/0318960 A1 | 12/2009 | Burkhart |
| 2009/0326579 A1 | 12/2009 | Anderhub et al. |
| 2010/0063542 A1 * | 3/2010 | van der Burg ..... A61B 17/0401 606/232 |
| 2010/0069974 A1 | 3/2010 | Oren et al. |
| 2010/0094355 A1 | 4/2010 | Trenhaile |
| 2010/0100127 A1 | 4/2010 | Trenhaile |
| 2010/0114123 A1 | 5/2010 | Nason |
| 2010/0121337 A1 | 5/2010 | Pandya |
| 2010/0121338 A1 | 5/2010 | Pandya |
| 2010/0121348 A1 | 5/2010 | Van Der Burg et al. |
| 2010/0121349 A1 | 5/2010 | Meier et al. |
| 2010/0121354 A1 | 5/2010 | Pandya |
| 2010/0121375 A1 | 5/2010 | Pandya |
| 2010/0137889 A1 | 6/2010 | Oren et al. |
| 2010/0160962 A1 | 6/2010 | Dreyfuss et al. |
| 2010/0179592 A1 | 7/2010 | Martinek et al. |
| 2010/0198235 A1 | 8/2010 | Pierce et al. |
| 2010/0198258 A1 | 8/2010 | Heaven et al. |
| 2010/0118254 A1 | 9/2010 | Pandya |
| 2010/0228254 A1 * | 9/2010 | Pandya ............... A61B 17/1684 606/80 |
| 2010/0249806 A1 | 9/2010 | Oren et al. |
| 2010/0249834 A1 | 9/2010 | Oren et al. |
| 2010/0292733 A1 | 11/2010 | Hendrickson et al. |
| 2010/0218139 A1 | 12/2010 | Beauchamp |
| 2010/0312249 A1 | 12/2010 | Sanders |
| 2010/0324575 A1 | 12/2010 | Chan |
| 2010/0331881 A1 | 12/2010 | Hart |
| 2011/0009867 A1 | 1/2011 | Oren et al. |
| 2011/0009884 A1 | 1/2011 | Kaplan |
| 2011/0022087 A1 | 1/2011 | Cerundolo |
| 2011/0087245 A1 | 4/2011 | Weinert et al. |
| 2011/0106124 A1 | 5/2011 | Beauchamp |
| 2011/0112550 A1 | 5/2011 | Heaven |
| 2011/0112576 A1 | 5/2011 | Nguyen |
| 2011/0118757 A1 | 5/2011 | Pierce |
| 2011/0118762 A1 | 5/2011 | Dooney, Jr. |
| 2011/0152928 A1 | 5/2011 | Colleran et al. |
| 2011/0208198 A1 | 8/2011 | Anderson |

(56) References Cited

U.S. PATENT DOCUMENTS

| | | |
|---|---|---|
| 2011/0224762 A1 | 9/2011 | Lombardo |
| 2011/0264140 A1 | 10/2011 | Lizardi et al. |
| 2012/0053626 A1 | 3/2012 | Koepke |
| 2012/0143224 A1 | 6/2012 | Chan |
| 2012/0179199 A1 | 7/2012 | Hernandez et al. |
| 2012/0197575 A1 | 8/2012 | Saveliev et al. |
| 2012/0209279 A1 | 8/2012 | Snyder |
| 2012/0245634 A1 | 9/2012 | Kaplan |
| 2013/0096611 A1 | 4/2013 | Sullivan |
| 2013/0103083 A1 | 4/2013 | Baird |
| 2013/0123809 A1 | 5/2013 | Murphy et al. |
| 2013/0123840 A1 | 5/2013 | Murphy et al. |
| 2013/0123842 A1 | 5/2013 | Chan et al. |
| 2013/0123843 A1 | 5/2013 | Chan et al. |
| 2013/0144335 A1 | 6/2013 | Sandow |
| 2013/0190871 A1 | 7/2013 | Markarian |
| 2013/0197577 A1 | 8/2013 | Wolf |
| 2013/0197578 A1 | 8/2013 | Gregoire |
| 2013/0204299 A1 | 8/2013 | Mantovani |
| 2013/0267998 A1 | 10/2013 | Vijay |
| 2013/0345711 A1 | 12/2013 | Mehta |
| 2014/0046369 A1 | 2/2014 | Heaven |
| 2014/0114411 A1 | 4/2014 | Baird |
| 2014/0134802 A1 | 5/2014 | Lin |
| 2014/0172016 A1 | 6/2014 | Housman |
| 2014/0303625 A1 | 10/2014 | Sholey |
| 2014/0343605 A1 | 11/2014 | Lunn |
| 2014/0364905 A1 | 12/2014 | Lunn |
| 2015/0119937 A1 | 4/2015 | Lunn |
| 2015/0150551 A1 | 6/2015 | Paulk |
| 2015/0196388 A1 | 7/2015 | Housman |

FOREIGN PATENT DOCUMENTS

| | | |
|---|---|---|
| WO | 2011/008607 | 1/2011 |
| WO | 2012/007941 | 1/2012 |
| WO | 2013/027209 | 2/2013 |
| WO | 2013/027210 | 2/2013 |

OTHER PUBLICATIONS

"Arthroscopic Shoulder Repair Using the Smith & Nephew FOOTPRINT PK Suture Anchor" (2008) Smith & Nephew, Inc., 12pgs.
"CurvTek Bone Tunneling System" (2000) Arthrotek, Inc., 6pgs.
"The OPUS® AutoCuff® System Featuring SpeeScrew™ for Rotator Cuff Repair" (2009) Arthrocare Corporation, 8pgs.
ArthroCare Sports Medicine International, Products: SpeedStitch MagnumWire Suture Cartridges, (3ea: white & co-braid), http://www.arthrocaresportsmedicine.com/products/view/435 Sep. 24, 2012, 1pg.
ArthroCare Sports Medicine International, Products: SpeedStitch Suturing Device, http://www.arthrocaresportsmedicine.com/products/view/431 Sep. 24, 2012, 1 pg.
Baums, et al. "Tendon-bone contact pressure and biomechanical evaluation of a modified suture-bridge technique for rotator cuff repair" Knee Surg Sports Traumatol Arthrosc (2010) 18:992-998.
Dermirhan, et al. "Current Concept: Arthroscopic Transosseous Equivalent Suture Bridge Rotator Cuff Repair" (2012) 109-115, Springer-Verlag Berlin Heidelberg.
Lorbach and Tompkings "Rotator Cuff: Biology and Current Arthroscopic Techniques" Knee Surg Sports Traumatol Arthrosc, Springer-Verlag, published online: Jan. 21, 2012, 9pgs.
Maguire, et al. "Biomechanical Evaluation of Four Different Transosseous-equivalent/suture Bridge Rotator Cuff Repairs" Knee Surg Sports Traumatol Arhtrosc (2011) 19:1582-1587.
Park, et al. "Part I: Footprint Contact Characteristics for a Transosseous-equivalent Rotator Cuff Repair Technique Compared with a Double-row Repair Technique" J.Shoulder Elbow Surg (2007) 16(4):461-468.
Upper Limb Surgery Info., Adelaide—Wakefield Orthopaedic Clinic, SA, http://www.woc.com.au/upper-limb-research.html, Jan. 30, 2012, 4pgs.
VERSALOK the Next Generation in Rotator Cuff Repair, (2007) DePuy Mitek, Inc., www.depuymitek.com, 18pgs.
European Search Report for EP 12846903.8, dated Jun. 25, 2015, 7 pp.
ISR/WO for PCT/US2012/064669, dated Nov. 12, 2012, 14 PP.
Multifix's PEEK 5.5mm and 6.5mm Knotless Implants Technique Guide, ArthroCare Corporation, www.smith-nephew.com, Jul. 2015, 8 pp.
Multifix PEEK Knotless Fixation Implants, ArthroCare Corporation, www.smith-nephew.com, Aug. 2015, 6 pp.
Achilles Speedbridge Surgical Technique, Arthrex, Inc., www.arthrex.com, 2013, 6 pp.
Achilles Suturebridge Surgical Technique, Arthrex, Inc., www.arthrex.com, 2014, 6 pp.
Massive Rotator Cuff Repair and Augmentation using the Speedbridge and ArthroFlex Dermal Matrix Surgical Technique, Arthrex, Inc., www.arthrex.com, 2012 4 pp.
Arthrex is Reaching New Heights in Rotator Cuff Repair, Arthrex, Inc. www.arthrex.com, 2007, 8 pp.
Speedbridge and SpeedFix Knotless Rotator Cuff Repair using the SwiveLock C and FiberTape Surgical Technique, Arthrex, Inc. www.arthrex.com, 2013, 8 pp.
SutureBridge Double Row Rotator Cuff Repair Surgical Technique, Arthrex, Inc. www.arthrex.com, 2013, 6 pp.
Quattro Shoulder System—Innovative Rotator Cuff Solutions, Cayenne Medical, Inc., www.cayennemedical.com, 6 pp.
Shoulder Restoration System—PopLok Knotless Suture Anchor Surgical Technique, ConMed Linvatec, www.linvatec.com, 2013, 8 pp.
The Next Generation in Rotator Cuff Repair, DePuy Mitek, Inc., www.depuymitek.com, 2007, 18 pp.
Footprint PK Suture Anchor, Arthroscopic Shoulder Repair Using the Smith & Nephew Footprint PK Suture Anchor Technique Guide, Smith & Nephew, Inc., www.smith-nephew.com, Apr. 2008, 12 pp.
Mall, Nathan A., et al. "Transosseous-Equivalent Rotator Cuff Repair: A Systematic Review on the Biomechanical Importance of Tying the Medial Row", The Journal of Arthroscopic and Related Surgery, vol. 29, No. 2, Feb. 2013, pp. 377-386.
Sharc-FT and Taylor Stitcher Transosseus Devices for Fast Rotator Cuff Repair Surgical Technique, NCS Lab Medical Devices Factory, 12 pp.
Comprehensive Product Offerings for Your Rotator Cuff Repair, Smith&Nephew, Inc., www.smith-nephew.com, Jul. 2015, 12 pp.
OPUS AutoCuff, Magnum X Knotless Fixation Implant with Independent Tensioning, ArthroCare Sports Medicine, arthrocaresportsmedicine.com, 2009, 2 pp.
The OPUS TwinLock Knotless Fixation System, ArthroCare Sports Medicine, arthrocaresportsmedicine.com, 2010, 2 pp.
The OPUS AutoCuff System for Rotator Cuff Repair, ArthroCare Sports Medicine, arthrocaresportsmedicine.com, 2006, 8 pp.
BioRaptor—Knotless Suture Anchor, Smith&Nephew, Inc., www.smith-nephew.com, Apr. 2010, 6 pp.
Footprint PK Arthroscopic Shoulder Repair Using the Smith &Nephew FOOTPRINT PK Suture Anchor Technique Guide, Smith &Nephew, Inc., www.smith-nephew.com, Apr. 2008, 12 pp.
CinchLock SS (Sports Sheath) Knotless Labrum Restoration Surgical Technique, Pivot Medical, Inc., 6 pp.
ReelX STT Knotless Anchor System, Stryker, www.stryker.com, 2010, 4 pp.
Dr. S.D. Gerber Double Row Method Surgical Technique, Stryker, www.stryker.com, 2010, 12 pp.
ArthroTunneler TunnelPro System Transosseous Rotator Cuff Repair, Tornier, Inc., www.tornier.com, 2012, 6 pp.
Quickdraw Knotless Suture Anchor System Surgical Technique, ArthroCare Corporation, www.arthrocare.com, 2011, 28 pp.

\* cited by examiner

KNOTLESS SOFT TISSUE ATTACHMENT

CROSS-REFERENCE TO RELATED APPLICATIONS

This application is a continuation-in-part of U.S. patent application Ser. No. 13/674,837, filed Nov. 12, 2012, which claims the benefit of U.S. Provisional Application No. 61/560,694, filed Nov. 16, 2011, and U.S. Provisional Application No. 61/597,138, filed Feb. 9, 2012, all of which are hereby incorporated by reference.

FIELD OF THE INVENTION

The invention relates to devices and methods to transosseously attach soft tissue to bone.

BACKGROUND

A variety of surgical procedures require the attachment of something relative to a surgical site. For example, in surgery relating to the skeletal system, it is often advantageous to attach soft tissue, suture, implants, and/or other items in or adjacent to a joint. For example, ligaments, tendons, fascia, other capsular material, and/or muscle may be attached to an adjacent bone to affect a repair of a joint. Such joints may include any joint in a patient's body such as the joints of the hands and feet, ankle, wrist, knee, elbow, hip, shoulder, and spine. For example, it is often advantageous to pass a suture through a portion of a bone to form a transosseous attachment to the bone.

SUMMARY

Examples of the invention provide devices and methods to transosseously attach soft tissue to bone.

In one example of the invention, a method of attaching soft tissue to bone includes forming a bone tunnel through a bone, the bone tunnel having at least first and second spaced apart openings at the surface of the bone; engaging a knotless suture anchor with a suture to form a suture construct securing soft tissue to the bone wherein the suture construct extends from the soft tissue to the first opening, through the first opening, through the bone tunnel, through the second opening, and outside of the bone tunnel to the soft tissue.

In another example of the invention, a method of making a transosseous repair of a rotator cuff includes forming a bone tunnel through a humeral bone, the bone tunnel having at least first and second spaced apart openings at the surface of the humeral bone; forming a suture construct securing a portion of the rotator cuff to the bone, without tying any knots, wherein the suture construct extends from the rotator cuff to the first opening, through the first opening, through the bone tunnel, through the second opening, and outside of the bone tunnel to the rotator cuff.

In another example of the invention, a transosseous rotator cuff repair construct includes a suture securing a portion of the rotator cuff to the bone, without tying any knots, wherein the suture extends from the rotator cuff to a first opening of a bone tunnel through a humeral bone, through the first opening, through the bone tunnel, through a second opening of the bone tunnel spaced from the first opening on the surface of the humeral bone, and outside of the bone tunnel to the rotator cuff.

BRIEF DESCRIPTION OF THE DRAWINGS

Various examples of the present invention will be discussed with reference to the appended drawings. These drawings depict only illustrative examples of the invention and are not to be considered limiting of its scope.

DESCRIPTION OF THE ILLUSTRATIVE EXAMPLES

Minimally invasive surgery is surgery used to gain access to deeper parts of the human body through small incisions. Such surgery may range from mini-open surgery to arthroscopic surgery. Mini-open surgery is generally understood to mean surgery performed through small incision(s) under direct vision as opposed to arthroscopic (or endoscopic) surgery where surgery is performed through one or more stab incisions in which the arthroscope (or endoscope) is used for visualization. In arthroscopic surgeries, the size of the stab incisions generally range from 1 mm to 10 mm. The illustrative examples depict arthroscopic surgical techniques but it is to be understood that the techniques could be performed in any minimally invasive or open technique. The following illustrative examples depict implants and techniques to pass a suture through a portion of the head of the humeral bone at the shoulder of a human patient and fix the suture there to repair damaged soft tissue associated with the shoulder joint. Instruments and techniques according to the present invention may be used to anchor a suture to any bone, at surgical sites anywhere in a patient's body, and for any purpose. The terms "suture" and "suture strand" are used herein to mean any strand or flexible member, natural or synthetic, able to be passed through a bone tunnel and useful in a surgical procedure. The term "transverse" is used herein to mean to cross at an angle; i.e. not parallel. The term includes, but is not limited to right angles. The term "bight" is used herein to mean a bend or loop formed in the intermediate portion of a suture.

A human left shoulder joint is used to provide context for illustrative examples of a surgical technique. The subacromial space, between the humeral head and the undersurface of the acromion, is a potential space for surgical repair. This space is partially occupied by the subacromial bursa. Soft tissue layers overlie the shoulder joint. These layers define a soft tissue zone including the skin, subcutaneous tissue, muscles and bursal tissue. Instruments are inserted through the soft tissue zone via stab incisions and access canulae can be inserted through these stab incisions to facilitate the insertion and withdrawal of surgical instruments. The thickness of this soft tissue zone varies by patient and by location from a few millimeters to several centimeters.

Figure 1:
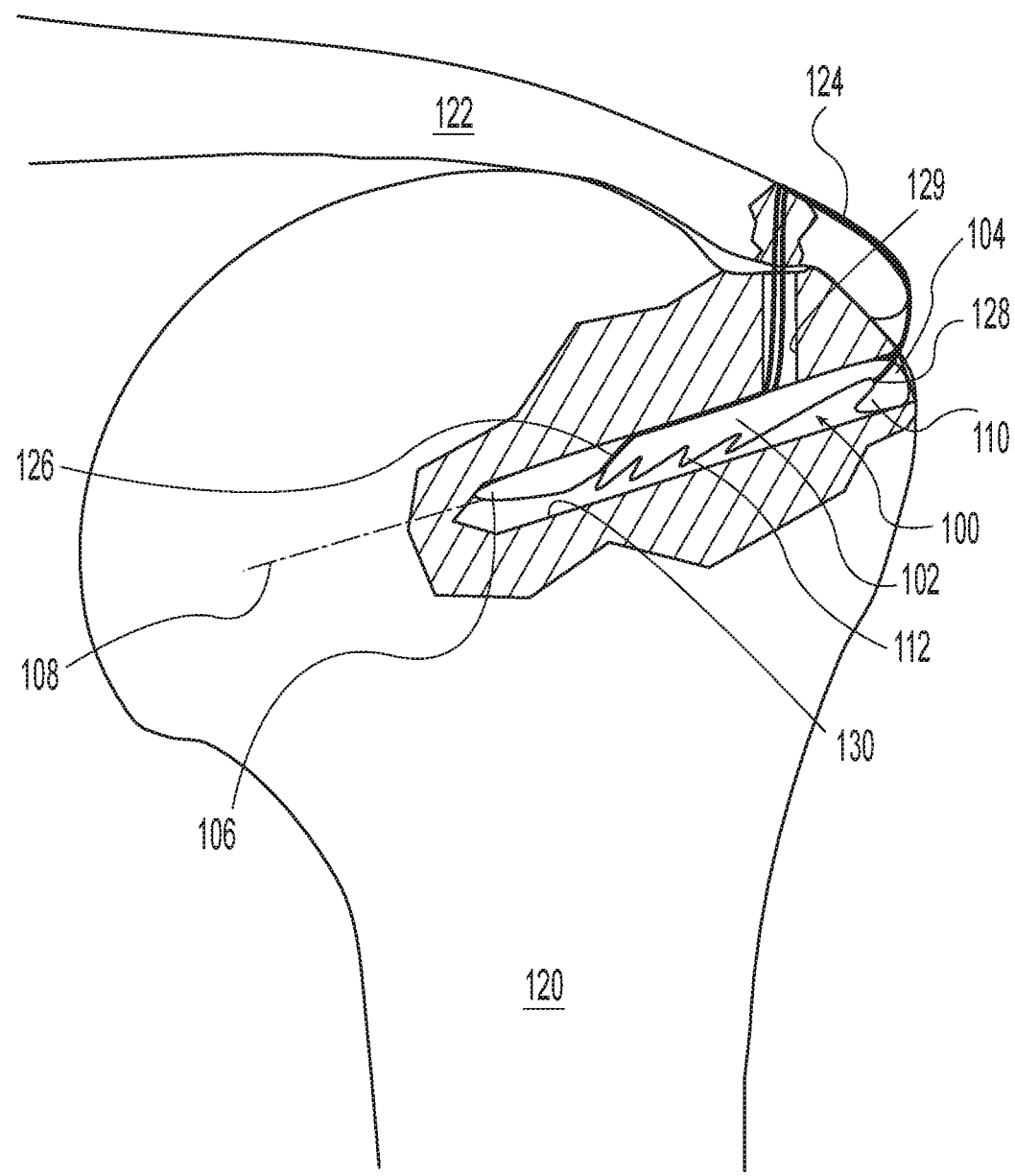
FIG. 1 is a partial side sectional view of an illustrative implant and method according to one example of the present invention.

Referring to FIG. 1 an osseous attachment device includes an implant 100 having an elongated shaft 102 extending from a proximal end 104 to a distal end 106 along an axis 108. The shaft 102 engages an elongated flexible strand to hold it relative to a bone. For example, FIG. 1 depicts a bone 120 and soft tissue 122 to be attached to the bone 120 adjacent a skeletal joint; e.g. a proximal humerus and a portion of a rotator cuff. An elongate flexible strand 124 such as a suture having first and second ends 126, 128 is passed through the soft tissue 122 and into the bone 120 at a desired attachment site. The implant 100 is inserted into the bone 120 to capture and retain the ends 126, 128 to hold the soft tissue 122 adjacent the bone 120.

For example, in a shoulder repair procedure, an elongate strand 124 in the form of at least one closed suture loop may be passed through the soft tissue 122 of the rotator cuff and the first end 126 of the loop placed in the bone 120 such as by placing it into a preformed tunnel or impacting it into the bone on a driver to simultaneously form a tunnel and insert the first end 126. In the illustrative embodiment of FIG. 1, the first end 126 is positioned in first tunnel 129. A hook 110 is formed adjacent the proximal end 104 of the implant 100 with a hook opening facing distally. The hook 110 is engaged with the second end 128 and inserted into the bone along a path intersecting the first end 126. The implant 100 and second end 128 may for example be impacted directly into the bone to simultaneously form a second tunnel 130 and insert the implant, or alternatively, they may be inserted into a preformed tunnel. In the illustrative embodiment of FIG. 1, one or more, optional barbs 112 project from the shaft 102 outwardly and distally. When the implant 100 intersects the first end 126, one or more of the barbs 112 engage the first end 126 such that when insertion of the implant 100 is complete, the implant 100 engages and secures both ends of the elongate strand 124 to retain the elongate strand in the bone 120 and secure the soft tissue 122 with the first end being secured distally and the second end being secured proximally. Alternatively, the barbs 112 may be omitted and the shaft 102 alone pass through the suture loop to constrain it within the bone. With the use of a preformed loop, the soft tissue attachment is accomplished without the need for the user to tie any knots.

Figure 2:
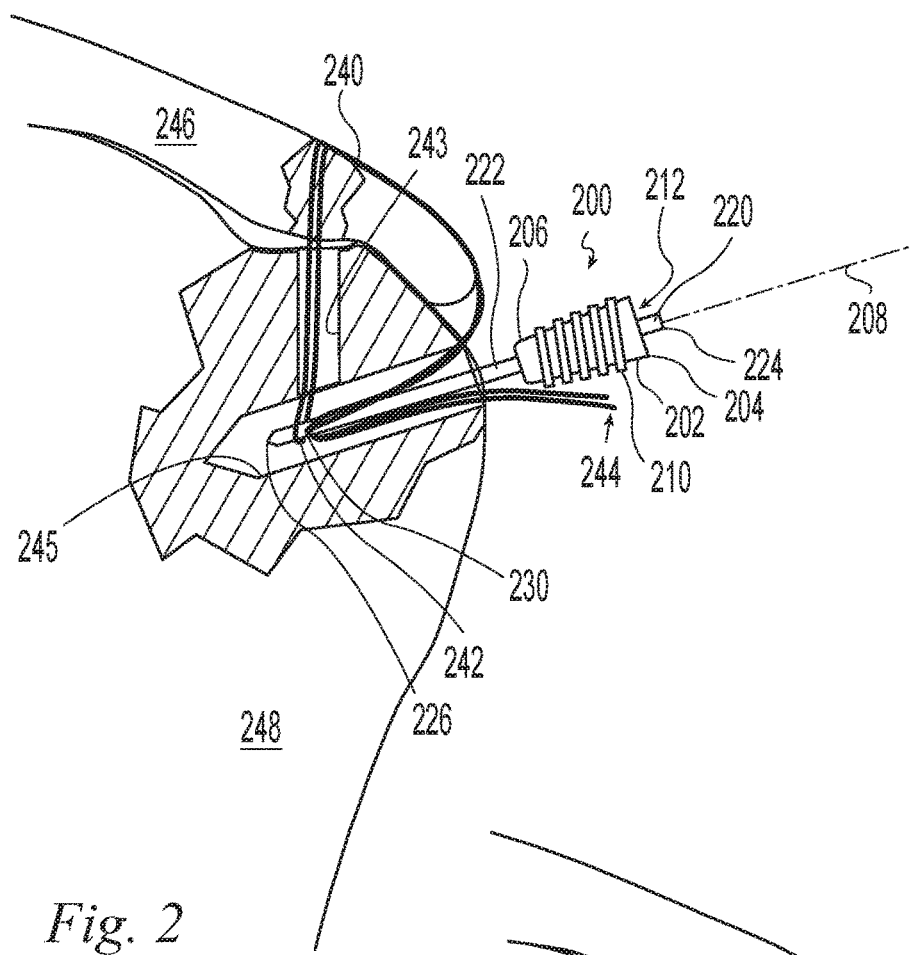
FIGS. 2 and 3 are partial side sectional views of an illustrative implant and method according to one example of the present invention.
Figure 3:
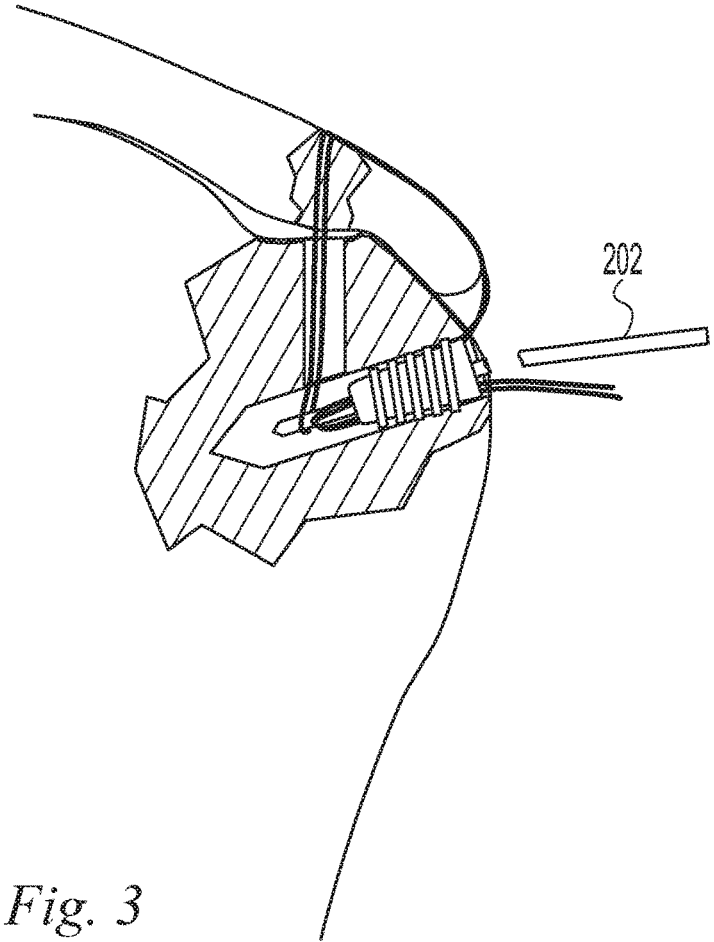

Referring to FIGS. 2 and 3, an osseous attachment device includes a locking implant 200 and an elongated member 220. In the illustrative embodiment of FIGS. 2 and 3, the implant 200 is in the form of an interference screw. The implant 200 includes an elongated tapered body 202 extending from a wider, proximal end 204 to a narrower, distal end 206 along an axis 208. A spiral thread 210 is formed on the exterior of the body 202 and the body includes an axial through passage 212. In the illustrative embodiment of FIG. 2, the separate elongated member 220 is in the form of a suture carrier that includes an elongated shaft 222 extending from a proximal end 224 to a distal end 226. The distal end 226 may be tapered or otherwise sharpened to ease insertion into bone. A transverse opening 230 is formed through the shaft near the distal end 226. An optional groove or reduced diameter region may be provided proximal of the opening 230 to ease in cutting or breaking the elongated member 220 to a desired length. The passage 212 of the implant and shaft 222 of the elongated member are sized for axial translating engagement. The elongated member 220 is used to capture the ends of an elongated flexible strand and the implant 200 is used to lock the elongated flexible strand to hold the elongated flexible strand adjacent to a bone.

For example, in a shoulder repair procedure, an elongate strand 240 in the form of at least one suture defining a first end 242 in the form of a loop, or bight, and having second ends 244, may be passed through the soft tissue 246 of the rotator cuff. The first end 242 is inserted into the bone 248 such as by placing it into a preformed tunnel 243 or impacting the elongate strand 240 into the bone on a driver to simultaneously form a first tunnel and insert the first end 242. The second ends 244 are passed through the transverse opening 230 of the elongated member 220 and the elongated member 220 and second ends 244 are inserted into the bone along a path that intersects the first end 242. The elongated member 220 and second ends 244 may for example be impacted directly into the bone to simultaneously form a second tunnel and insert elongated member 220 and second ends 244, or alternatively, they may be inserted into a preformed second tunnel 245. When the elongated member 220 intersects the first end 242, the distal end 226 of the elongated member 220 captures the first end 242 distally and prevents it from being withdrawn upwardly through the bone such that the first end 242 is retained distally in the bone. The second ends 244 may then be pulled to feed slack through the transverse opening 230 and tension the elongated strand 240 and approximate the soft tissue to the bone. The locking implant 200 is then engaged with the proximal end of the elongated member 220 and advanced into the bone 248. The locking implant 200 presses the elongated strand 240 against the bone in an interference engagement to lock the second ends 244 in the second tunnel 245. The locking implant also prevents the elongated member 220 from exiting the second tunnel 245 thus the locking implant locks both ends of the elongated strand 240 relative to the bone 248 and secures the soft tissue 246. The soft tissue attachment is accomplished without the need for the user to tie any knots.

Figure 4:
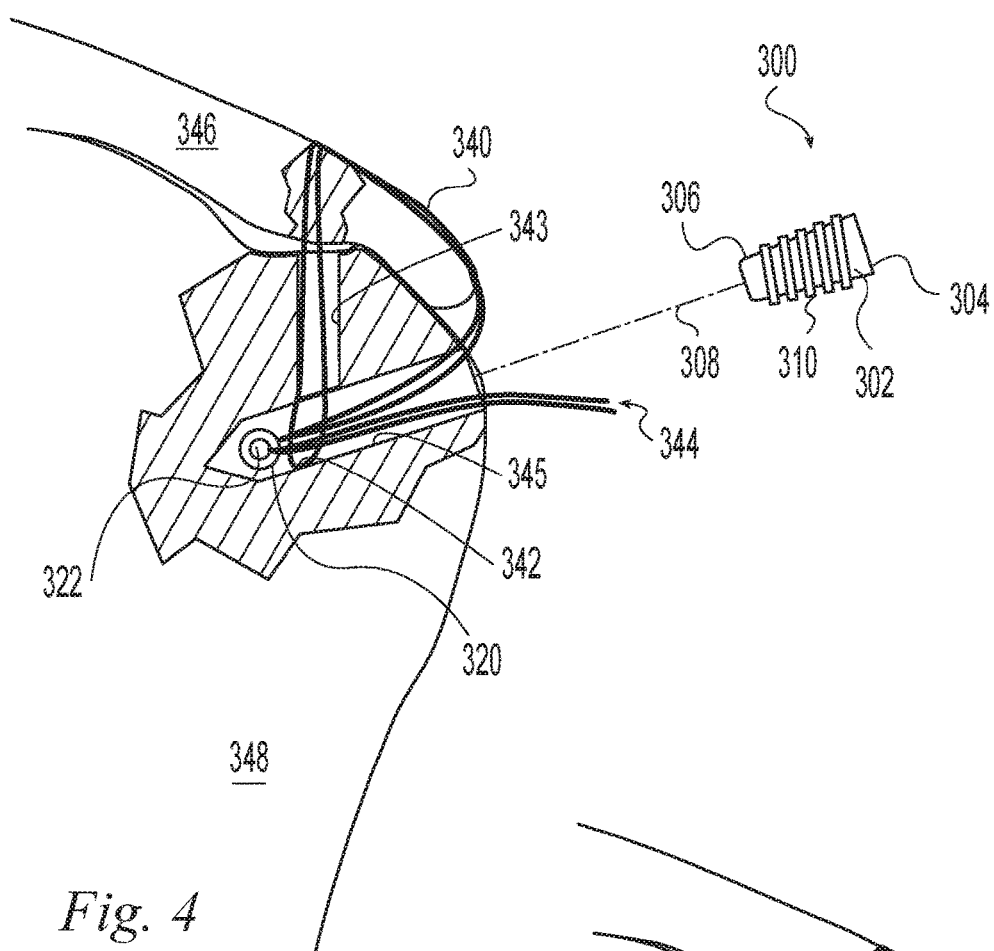
FIGS. 4 and 5 are partial side sectional views of an illustrative implant and method according to one example of the present invention.
Figure 5:
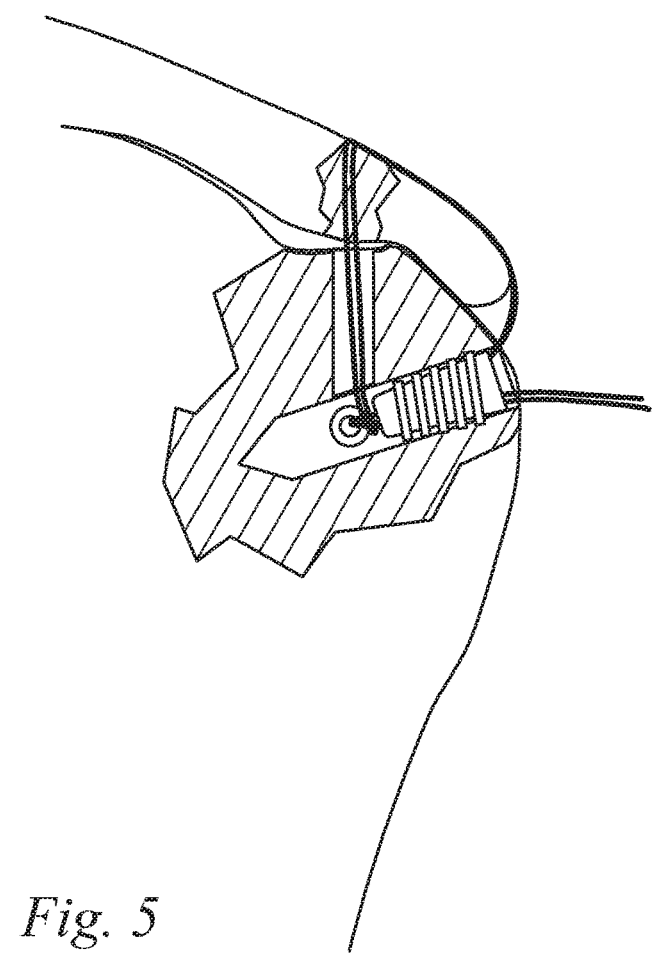

Referring to FIGS. 4 and 5, an osseous attachment device includes a locking implant 300 and a suture carrier 320 similar to that of FIGS. 2 and 3. In the illustrative embodiment of FIGS. 4 and 5, the implant 300 is in the form of an interference screw having a cylindrical body 302 extending from a proximal end 304 to a distal end 306 along an axis 308. A spiral thread 310 is formed on the exterior of the body 302. In the illustrative embodiment of FIGS. 4 and 5, the separate suture carrier 320 is in the form of a ring having an aperture 322. The suture carrier 320 is used to capture the ends of an elongated flexible strand and the locking implant 300 is used to lock the elongated flexible strand to hold the elongated flexible strand adjacent to a bone. While a suture carrier has been shown in the form of a ring it may have other forms such as a sphere, rod, or other suitable shape that can receive a suture in sliding relationship.

For example, in a shoulder repair procedure, as shown in FIGS. 4 and 5, an elongate strand 340 in the form of at least one suture defining a first end 342 in the form of a loop, or bight, and having second ends 344, may be passed through the soft tissue 346 of the rotator cuff. The first end 342 is inserted into the bone 348 such as by placing it into a preformed first tunnel 343 or impacting the elongate strand 340 into the bone on a driver to simultaneously form a tunnel and insert the first end 342. The second ends 344 are passed through the aperture 322 of the suture carrier 320 and the suture carrier 320 and second ends 344 are inserted into the bone along a path that intersects the first end 342. The suture carrier 320 and second ends 344 are passed through the loop of the first end 342. Applying tension to the elongated strand 340 causes the loop of the first end 342 to close around the second ends 344 and trap the suture carrier 320 in the bone such that the ends 342, 344 are retained in the bone. Further pulling on the second end 344 causes slack to feed through the suture carrier and tension the strand 340 to approximate the soft tissue to the bone. The locking implant 300 is then advanced into the bone 348. The locking implant 300 presses the elongated strand 340 against the bone in an interference engagement to lock the elongated strand 340 relative to the bone 348 and secure the soft tissue 346. The soft tissue attachment is accomplished without the need for the user to tie any knots.

Figure 6:
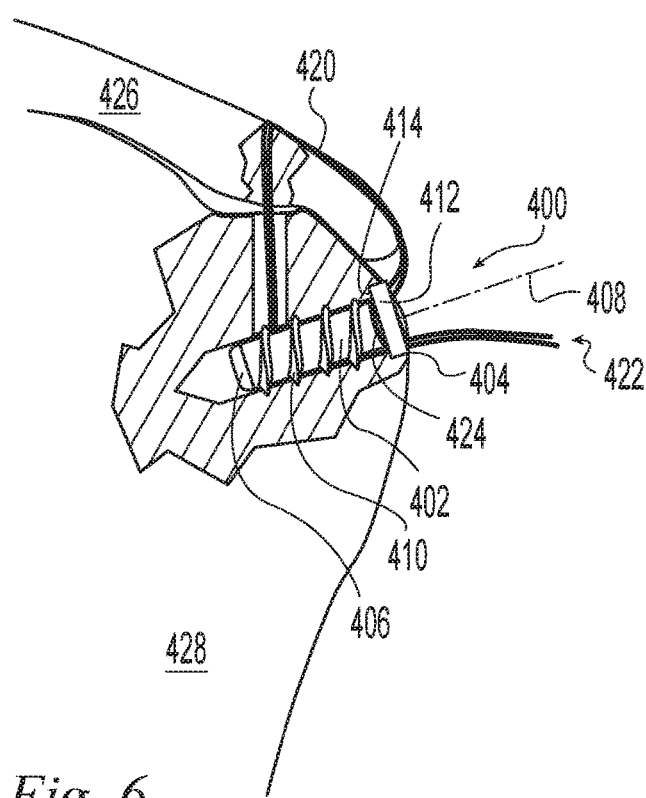
FIG. 6 is a partial side sectional view of an illustrative implant and method according to one example of the present invention.

Referring to FIG. 6, an osseous attachment device includes an implant 400. In the illustrative embodiment of FIG. 6, the implant 400 is in the form of an interference screw. The implant 400 includes an elongated body 402 extending from a proximal end 404 to a distal end 406 along an axis 408. A spiral thread 410 is formed on the exterior of the body 402. A head 412 is formed near the proximal end 404 and defines a distally facing shoulder 414 at the junction of the head 412 and body 402. The implant 400 is used to capture both ends of an elongated flexible strand 420 and hold the elongated flexible strand 420 adjacent to a bone.

For example, in a shoulder repair procedure, as shown in FIG. 6, an elongated strand 420 in the form of at least one suture having first ends 422 and a second end 424 defining a loop, may be passed through the soft tissue 426 of the rotator cuff. The first end 422 is inserted through the bone 428. The second end 424 is engaged with the distal end 406 of the implant 400. The first end 422 may be tensioned to remove slack and press the soft tissue against the bone. The distal end 406 of the implant 400 may be braced against the bone or engaged with the bone tunnel to facilitate tensioning the strand 420. The implant 400 is then driven into the bone to lock the ends 422, 424 relative to the bone. The second end 424 is trapped beneath the head 412 adjacent the shoulder 414 of the implant 400 and the first end is trapped between the thread 410 and bone 428.

Figure 7:
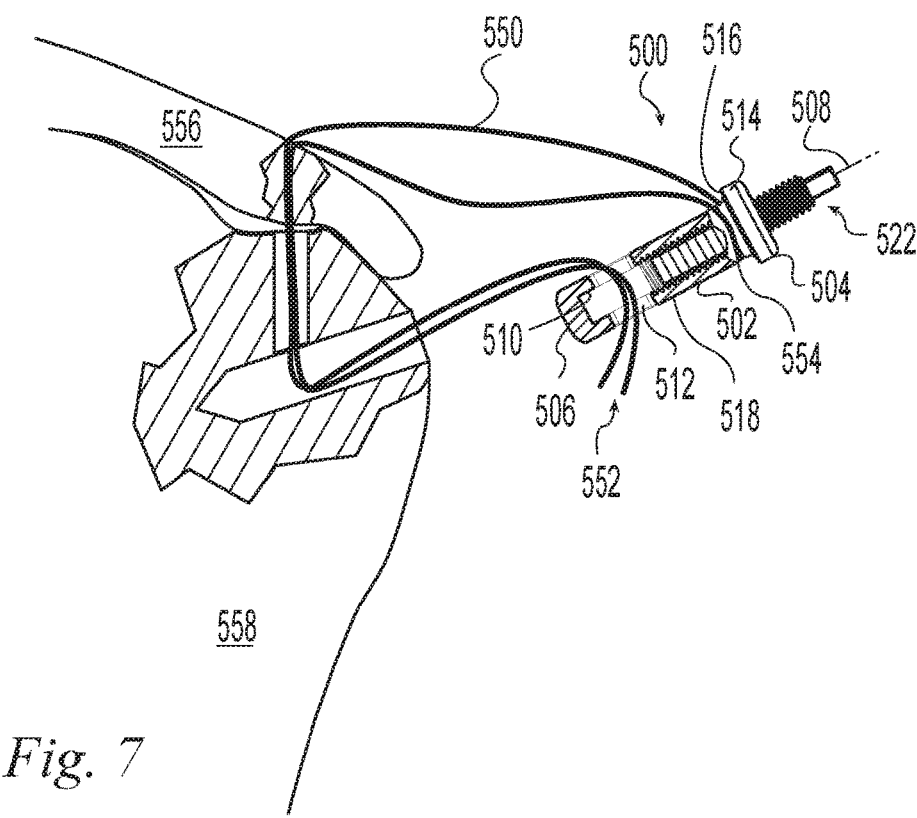
FIG. 7 is a partial side sectional view of an illustrative implant and method according to one example of the present invention.
Figure 8:
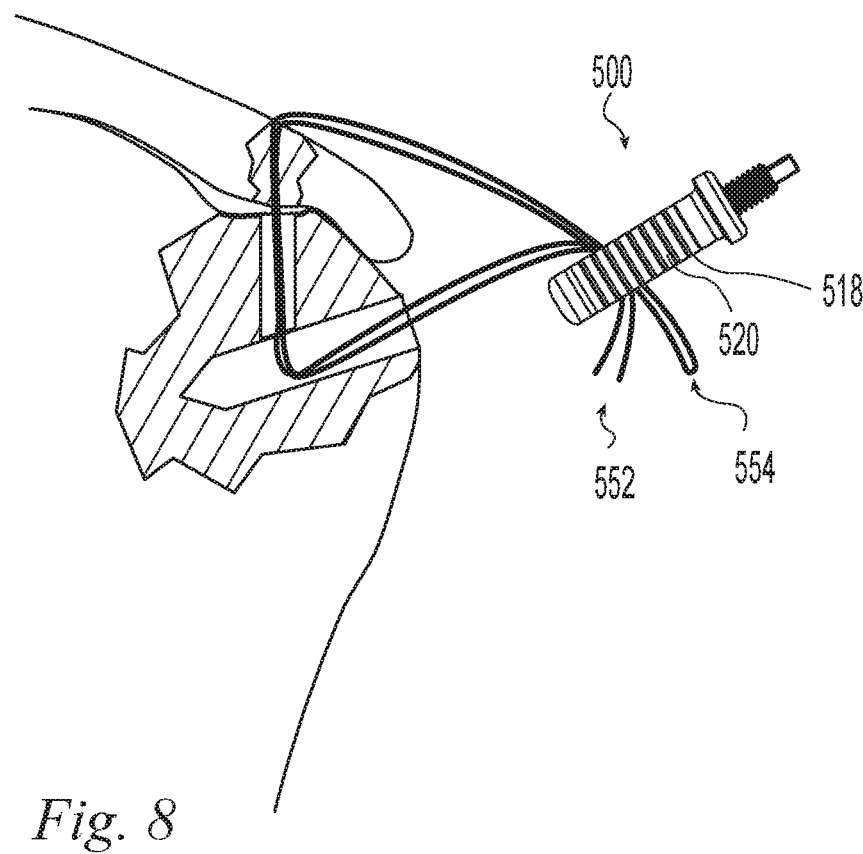
FIG. 8 is a partial side sectional view of the implant of FIG. 7 in use in an alternative method.

Referring to FIGS. 7 and 8, an osseous attachment device includes an implant 500. The implant includes an elongated body 502 extending from a proximal end 504 to a distal end 506 along an axis 508. An axial bore 510 extends into the body 502 proximally to distally. A transverse body aperture 512 extends through the body and intersects the axial bore 510. A head 514 is formed near the proximal end 504 and defines a distally facing shoulder 516 at the junction of the head 514 and body 502. The head 514 is interrupted by opposed grooves aligned with the aperture 512. Opposed flat surfaces 518 on the exterior of the body are aligned with the grooves and the aperture 512 and the grooves and flat surfaces 518 provide clearance to allow a suture to slide between the body 502 and a bone tunnel wall. The exterior of the body further includes annular projections 520 on opposite sides of the body 502 between the flat surfaces 518. The annular projections engage a bone tunnel wall to retain the implant 500 in the bone tunnel. The axial bore 510 is threaded proximally and receives a piston-like plunger 522 in axial threaded engagement such that the plunger is responsive to rotation to move between a first position in which the plunger 522 distal end is substantially not over-lapping the transverse body aperture 512 and a second position in which the plunger 522 overlaps at least a portion of the transverse body aperture 512.

The implant 500 is used to capture both ends of a strand and hold the strand adjacent to a bone. For example, in a shoulder repair procedure, as shown in FIG. 7, an elongated strand 550 in the form of at least one suture having a first end 552 and a second end 554 defining a loop, may be passed through the soft tissue 556 of the rotator cuff. The first end 552 is inserted through the bone 558. The second end 554 is looped around the body 502 such as by inserting the implant 500 through the loop of the second end 554 until the loop comes to rest against the shoulder 516. The first end 552 is passed through the aperture 512. The first end is then passed along the flat surface 518 and through the groove in the head. The implant 500 is inserted into the bone until the shoulder 516 abuts the bone 558. The first end 552 of the strand 550 is tensioned to remove slack and press the soft tissue against the bone. The plunger 522 is advanced toward the transverse aperture 512 until the distal end of the plunger 522 traps the second end 554 of the strand in the axial bore 510 such that the first end 552 is fixed distally in the aperture 512 and the second end 554 is trapped proximally under the shoulder 516.

FIG. 8 illustrates an alternative method of using the implant 500. In the illustrative method of FIG. 8, both ends 552, 554 of the suture are passed through the transverse aperture 512 of the implant 500 and along the flat surface 518 and through the groove in the head. The implant 500 is inserted into the bone until the shoulder 516 abuts the bone 558. The ends 552, 554 of the strand 550 are tensioned to remove slack and press the soft tissue against the bone. The plunger 522 is advanced toward the transverse aperture 512 until the distal end of the plunger 522 traps the ends 552, 554 of the strand distally in the aperture 512 intersecting the axial bore.

Figure 9:
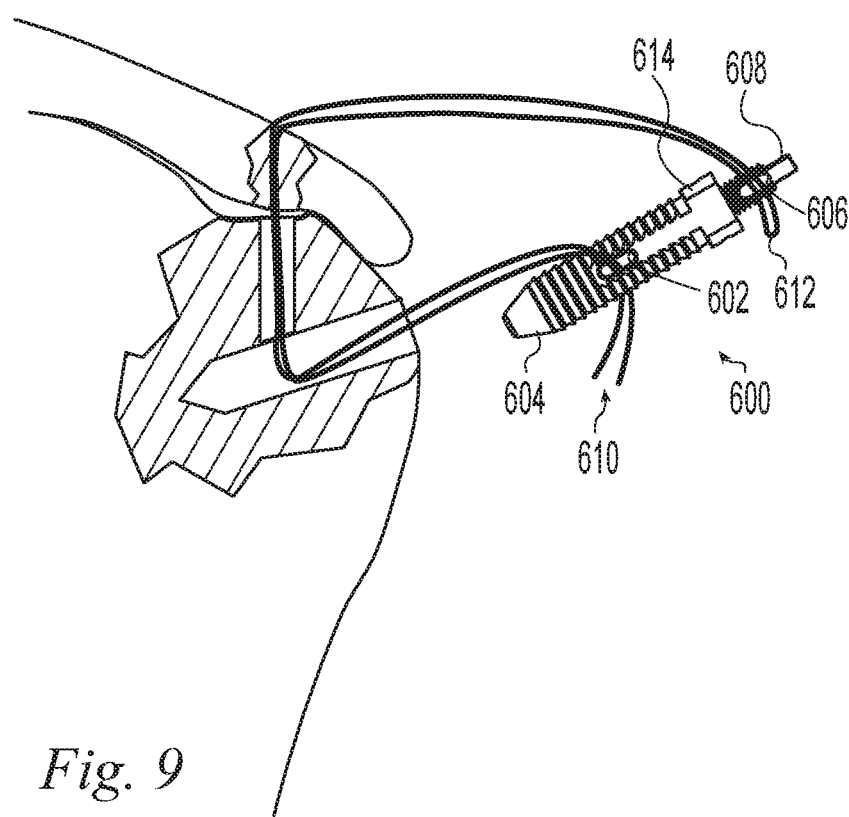
FIG. 9 is a partial side sectional view of an illustrative implant and method according to one example of the present invention.
Figure 10:
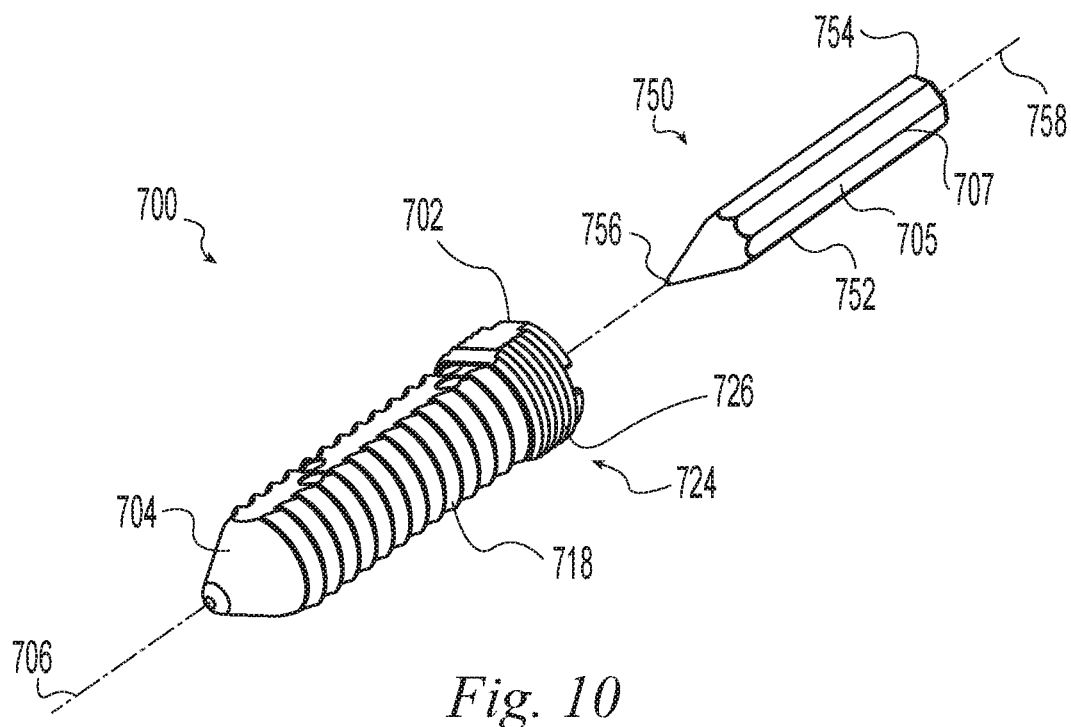
FIG. 10 is a perspective view of an illustrative implant according to one example of the present invention.
Figure 11:
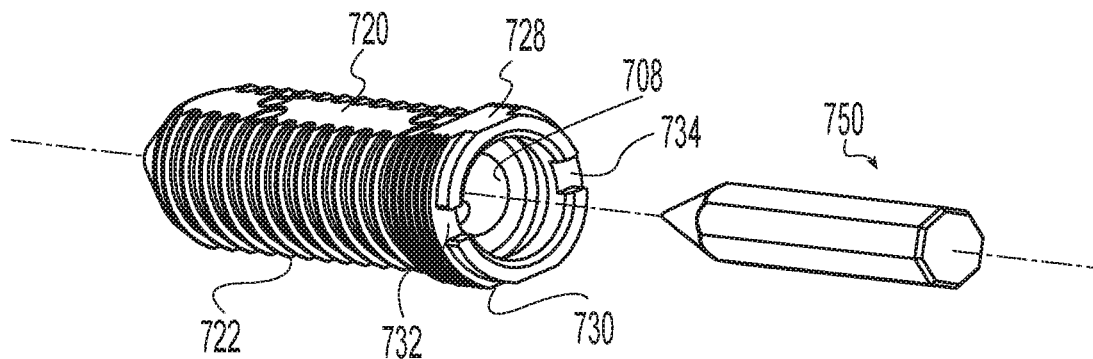
FIG. 11 is a perspective view of the implant of FIG. 10.
Figure 12:
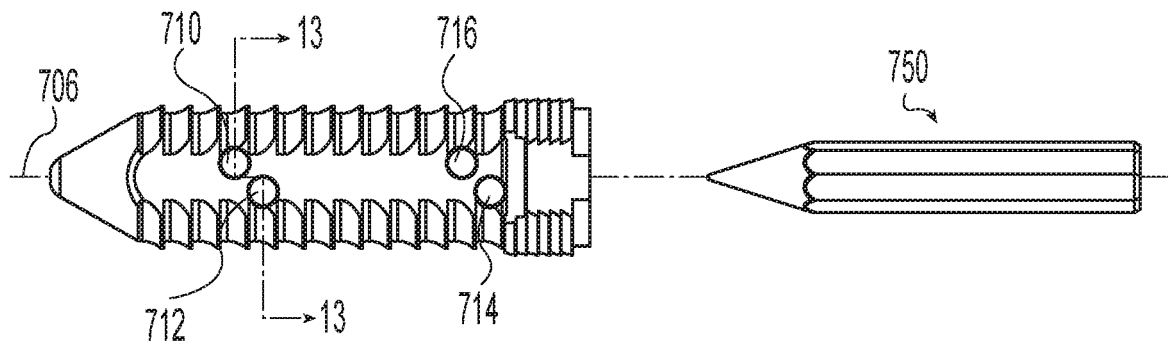
FIG. 12 is a side elevation view of the implant of FIG. 10.

Referring to FIG. 9, an osseous attachment device includes an implant 600 similar to that of FIGS. 7 and 8 except that the implant 600 of FIG. 9 includes a transverse aperture 602 through the implant body 604 and a transverse aperture 606 through the plunger 608 and the plunger 608 is advanced by pressing it into the body 604 rather than by threading. In this example, the first end 610 of the suture strand is passed through the body aperture 602 and the second end 612 is passed through the plunger aperture 606. When the plunger 608 is advanced in the body 604, the distal end of the plunger traps the first end 610 in the body aperture 602 and the plunger aperture 606 and head 614 trap the second end 612. The relationship between the plunger length and positions of the apertures 602, 606 may be adjusted to provide for simultaneous locking of the suture ends, distal locking of the first suture end 610 before proximal locking of the second suture end 612, or proximal locking of the second suture end 612 before distal locking of the first suture end 610.

Referring to FIGS. 10-15, an osseous attachment device includes an elongate implant body 700 and a plunger or piston 750 receivable in the body 700. The implant body extends from a proximal end 702 to a distal end 704 along an axis 706. An axial passage 708 extends into the body proximally to distally along the axis 706. First and second transverse apertures 710, 712, forming a distal aperture pair, extend through the body 700 distally and intersect the axial passage 708. The apertures 710, 712 are offset toward opposite sides of the axis 706 and the second aperture 712 is offset proximally from the first aperture 710. Third and fourth transverse apertures 714, 716, forming a proximal aperture pair, extend through the body 700 proximally and intersect the axial passage 708. The apertures 714, 716 are offset toward opposite sides of the axis 706 and the fourth aperture 716 is offset distally from the third aperture 714. The body 700 has radially extending ridges 718 that taper distally to aid in retaining the body in a tunnel. Opposed flats 720, 722 extend along opposite sides of the body 700 adjacent the apertures 710, 712, 714, 716 to provide clearance for suture ends extending alongside the body 700. A head 724 formed near the proximal end extends radially outwardly beyond the body diameter and includes radially extending ridges 726. Opposed flats 728, 730 extend along opposite sides of the head 724 in circumferential alignment with the body flats 720, 722 and apertures 710, 712, 714, 716 but spaced radially outwardly from the axis 706 farther than the flats 720 and 722. Alignment slots 732, 734 are formed on the distal end of the head to provide a rotational alignment keyway for a driver (not shown). The distal end 704 of the body tapers distally to ease insertion into a tunnel.

The plunger 750 includes an elongated body 752 extending from a proximal end 754 to a distal end 756 along an axis 758. The distal end of the plunger tapers distally to ease insertion into the body 700 and separate suture strands as will be more fully described below. The plunger 750 has faceted sides 705 defining elongated vertices, or ridges 707, at the intersection of adjacent facets. The plunger 750 is receivable in the passage 708 in axial translating relationship.

Figure 13:
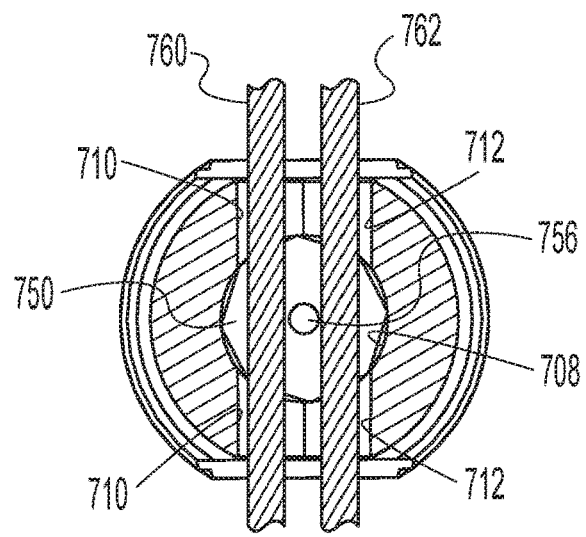
FIGS. 13-15 are sectional views taken along line 13-13 of FIG. 12 showing an aspect of the operation of the implant of FIG. 10.

One or more suture strands may be passed through the apertures 710, 712, 714, 716 and locked with the plunger 750. The plunger can lock any number of suture strands passing through any number of the apertures. Referring to FIG. 13, a suture strand 760, 762 has been passed through each of apertures 710 and 712. The plunger 750 has been advanced distally into the passage 708 until the distal end 756 of the plunger 750 is just short of touching the suture strands 760, 762. As can be seen in FIG. 13, since the apertures 710, 712 are offset outwardly from the axis 706, the tapered distal end 756 of the plunger, which is coaxial with axis 706, is directed between the strands 760, 762.

Figure 14:
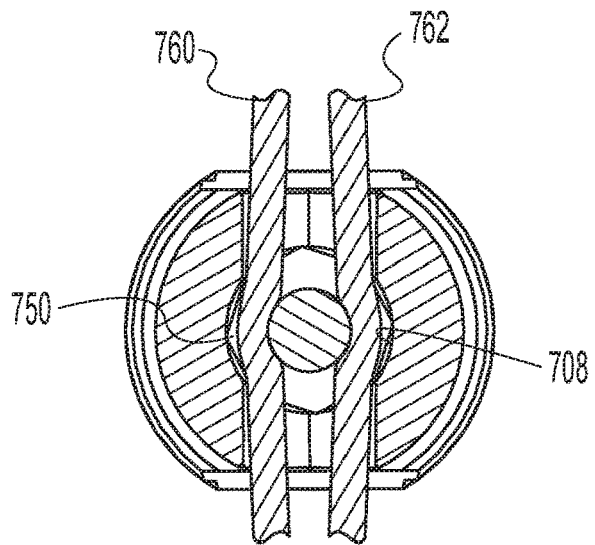

Referring to FIG. 14, the plunger has been advanced further distally and the distal end 756 has moved between the strands 760, 762 and begun pressing them outwardly toward the side wall of passage 708.

Figure 15:
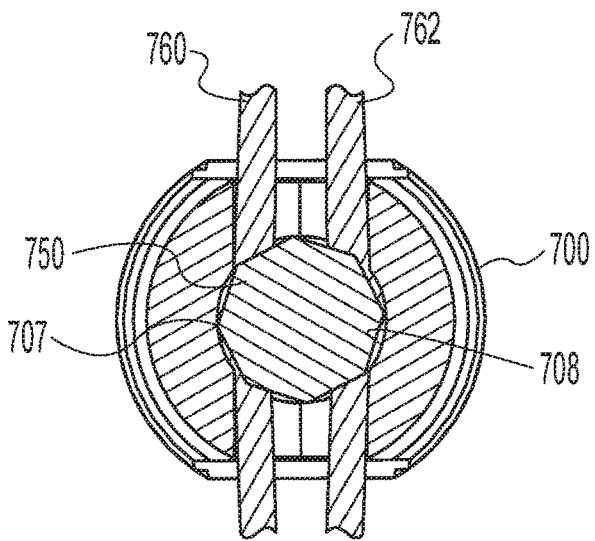

Referring to FIG. 15, the plunger 750 has been advanced fully into the passage 708 and tightly compresses the strands 760, 762 between the plunger sides and passage 708 such that the suture strands are locked firmly relative to the body 700. The plunger 750 presses the strands sideways into the sidewall of passage 708 and the suture strands are highly compressed by the ridges 707. Since the ridges 707 are able to slide smoothly over the sutures while compressing them, the advancing plunger 750 locks the suture strands without dragging the sutures axially along the passage 708 and therefore the suture strands are locked with little or no change in the suture tension.

FIGS. 16-19 depict an illustrative example of a method of using the implant of FIGS. 10-15 in a surgical procedure to secure a portion of a rotator cuff to a proximal humerus using knotless transosseous suture fixation.

Figure 16:
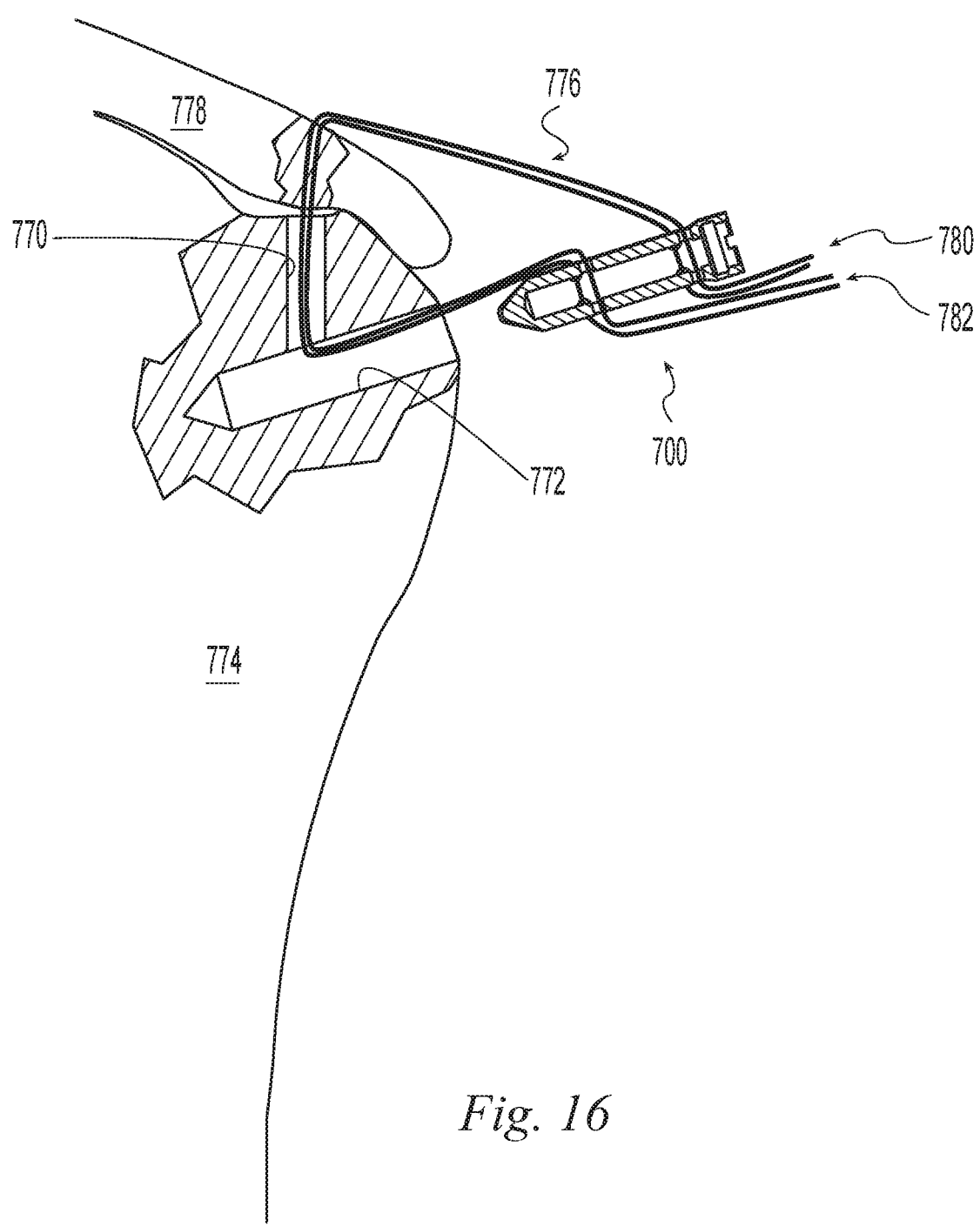
FIGS. 16-20 are partial side sectional views showing a method of using the implant of FIG. 10.

Referring to FIG. 16, first and second intersecting bone tunnels 770, 772 have been formed in the head of a humeral bone 774 of a shoulder joint. Suture strands 776 have been passed through the bone tunnels with first ends 780 exiting superiorly from the first bone tunnel and passing through a portion of the rotator cuff 778 and second ends 782 exiting laterally from the second bone tunnel 772. The first ends 780 have been passed through the proximal apertures 714, 716 of the implant body 700 and the second ends 782 have been passed through the distal apertures 710, 712. The second bone tunnel 772 is sized to be a press fit with the ridges 718 of the body 700.

Figure 17:
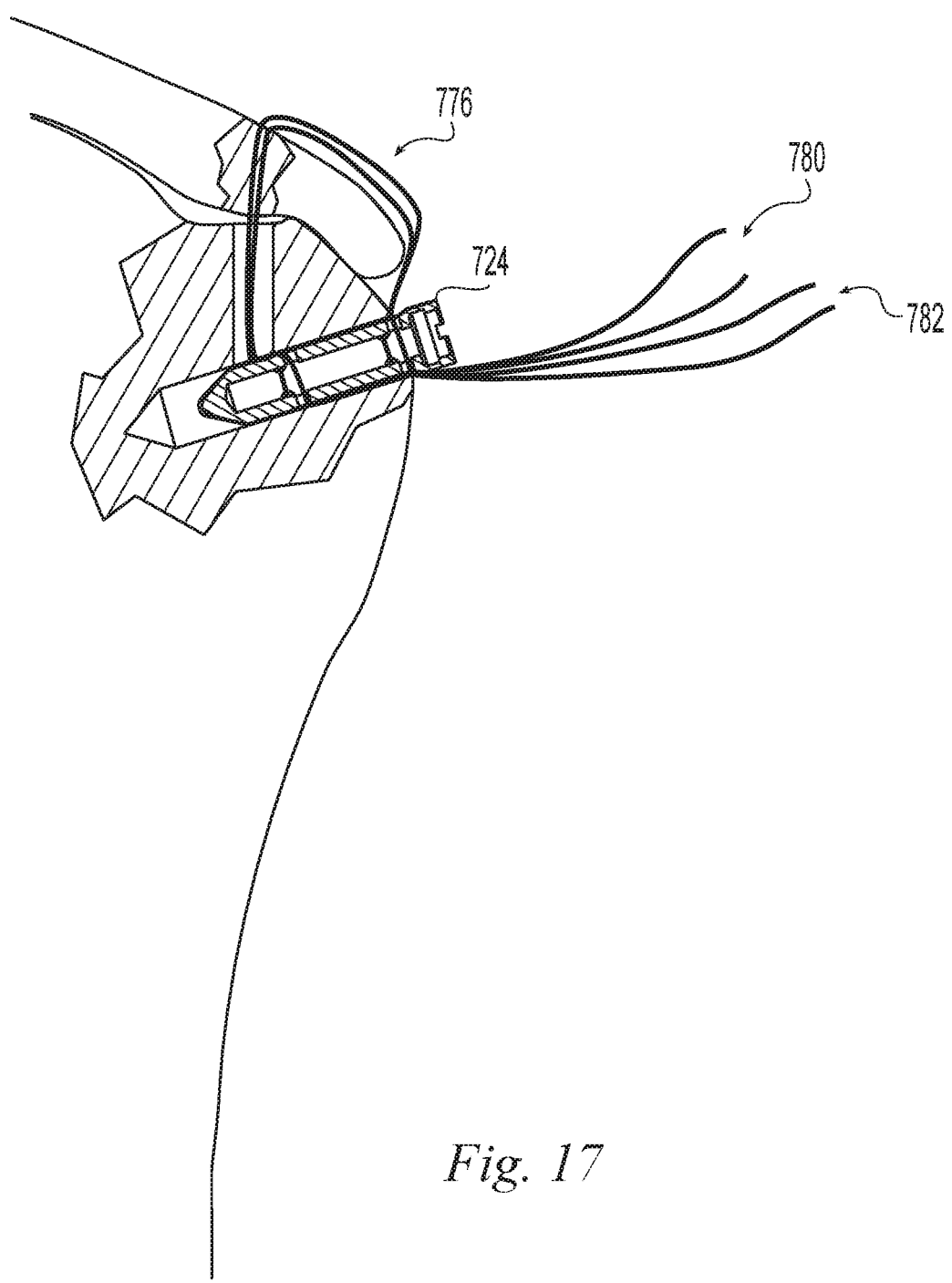

Referring to FIG. 17, the body 700 has been inserted into the second bone tunnel 772 up to the base of the head 724. In this position, the suture ends 780, 782 may be pulled to remove slack from the suture strands 776 and the strands will slide easily through the bone tunnels and implant body 700.

Figure 18:
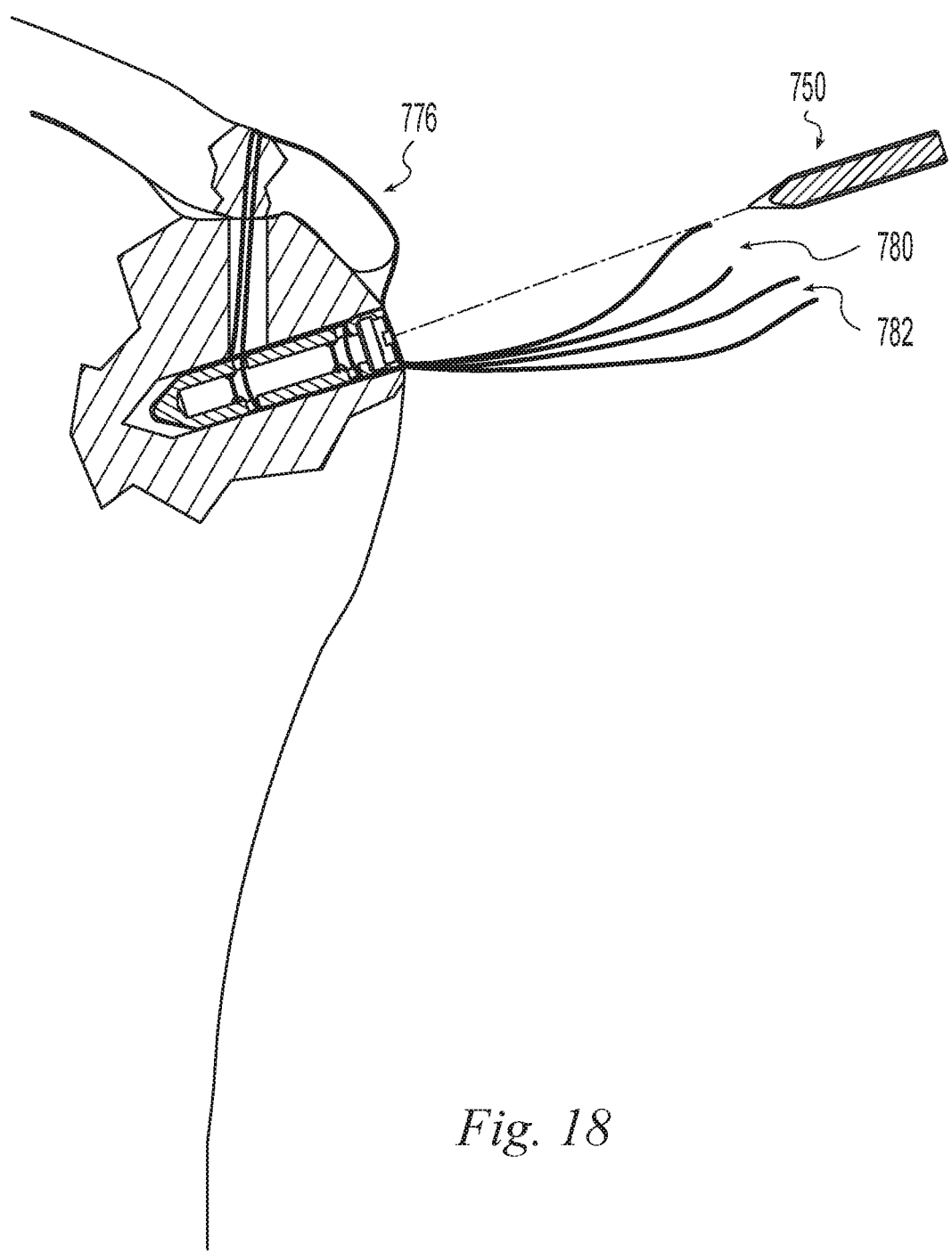

Referring to FIG. 18, the body 700 has been further inserted into the second bone tunnel 772 so that the head is flush with the bone and the head compresses the suture strands between the head and bone. Since the head 724 extends radially outwardly farther than the body 700, driving the head into the bone will compress the suture strands as shown in a provisionally locked state. In this state, the sutures will not slip easily but a user can supply sufficient force to the ends 780, 782 to overcome the frictional provisional lock and perform a final tensioning of the suture strands 776. The plunger 750 is shown aligned with the passage 708 ready to be inserted after final tensioning of the suture strands 776 is completed.

Figure 19:
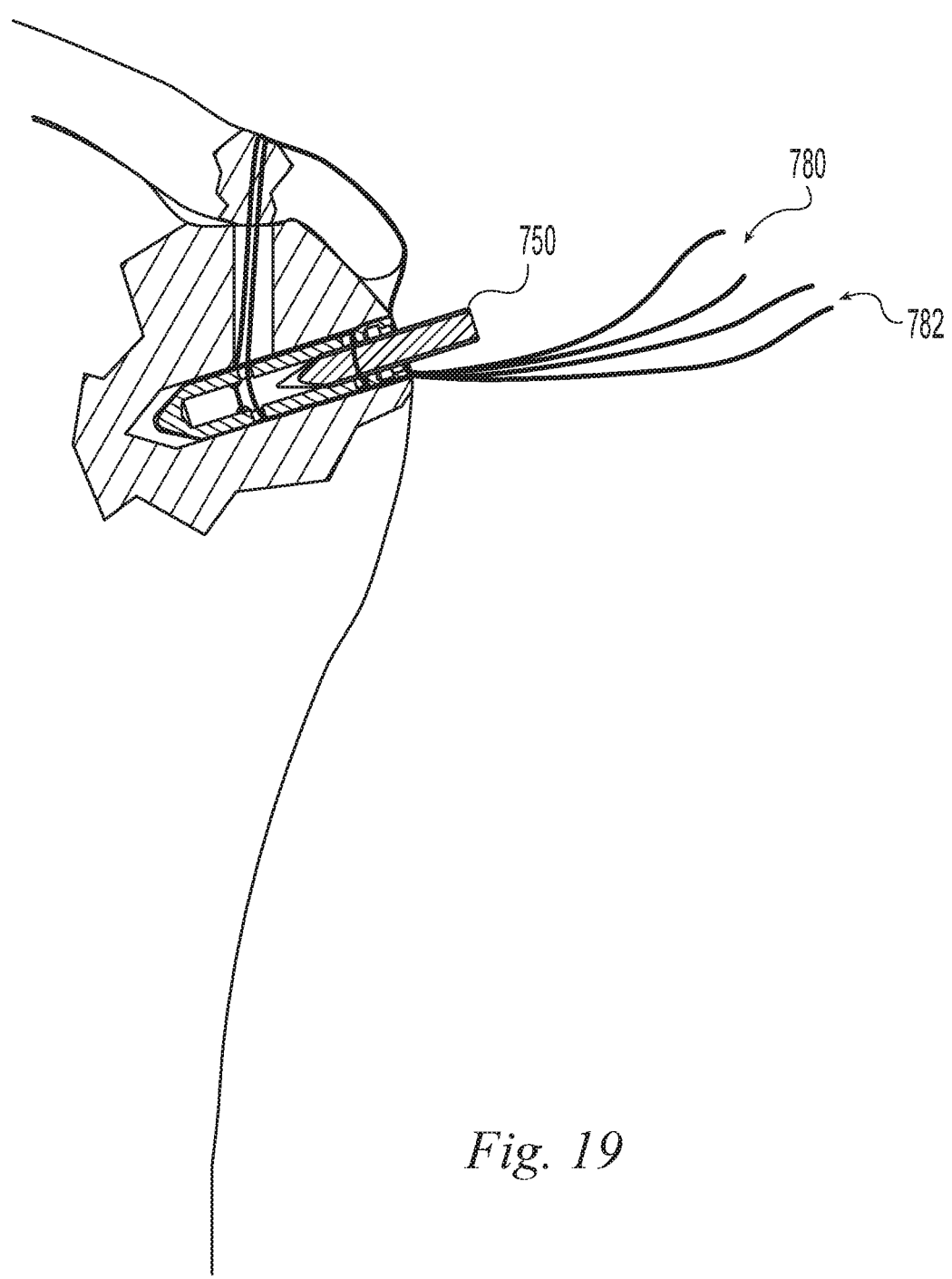

Referring to FIG. 19, the plunger 750 has been inserted partway into the passage 708 so that the suture ends 780 passing through the proximal aperture pair are locked but the suture ends 782 passing through the distal aperture pair can still be tensioned if desired. In this way the plunger 750 provides a sequential locking action relative to the proximal and distal apertures.

Figure 20:
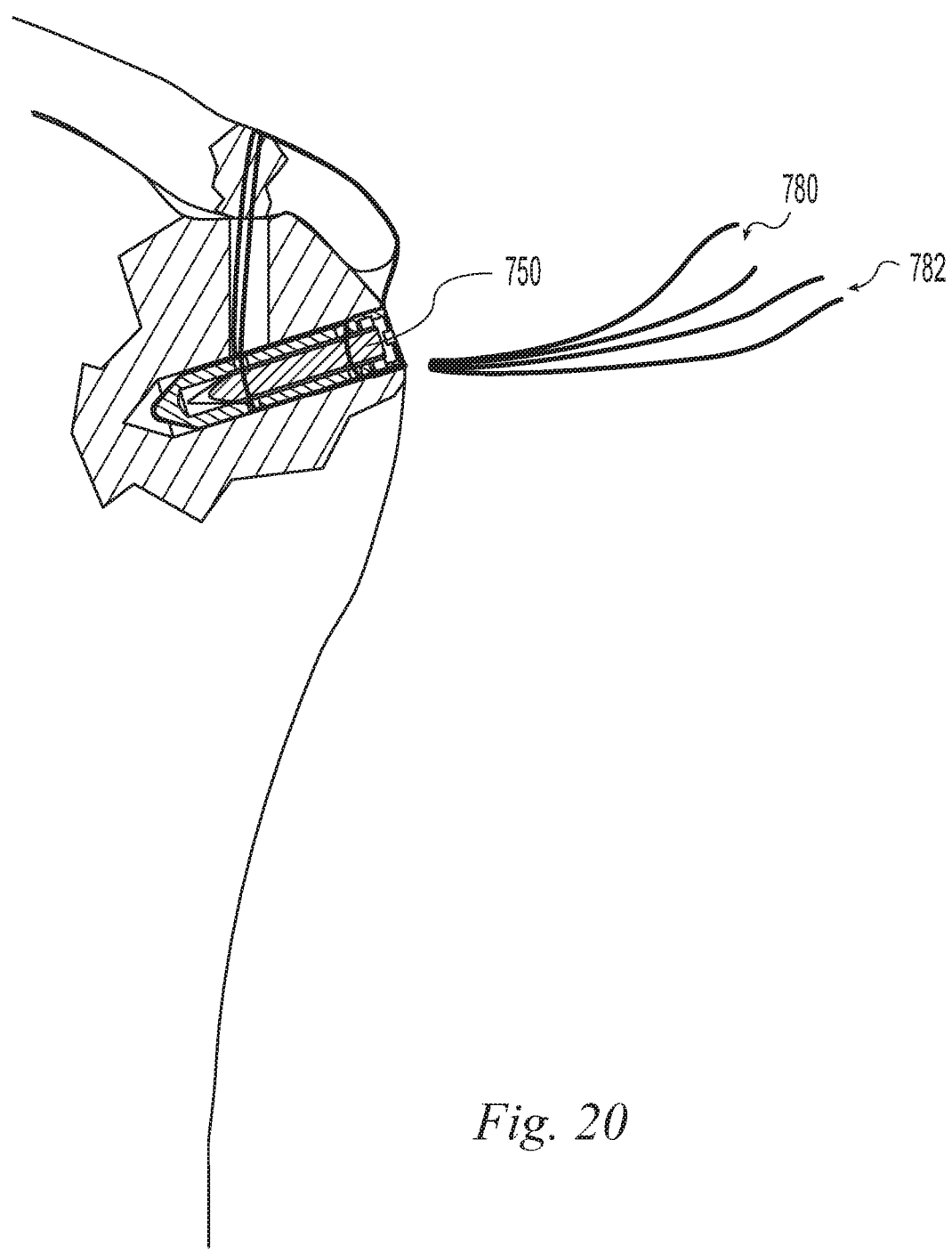

Referring to FIG. 20, the plunger 750 has been fully seated locking all of the suture strands and the loose suture ends have been cut off flush with the bone.

Figure 21:
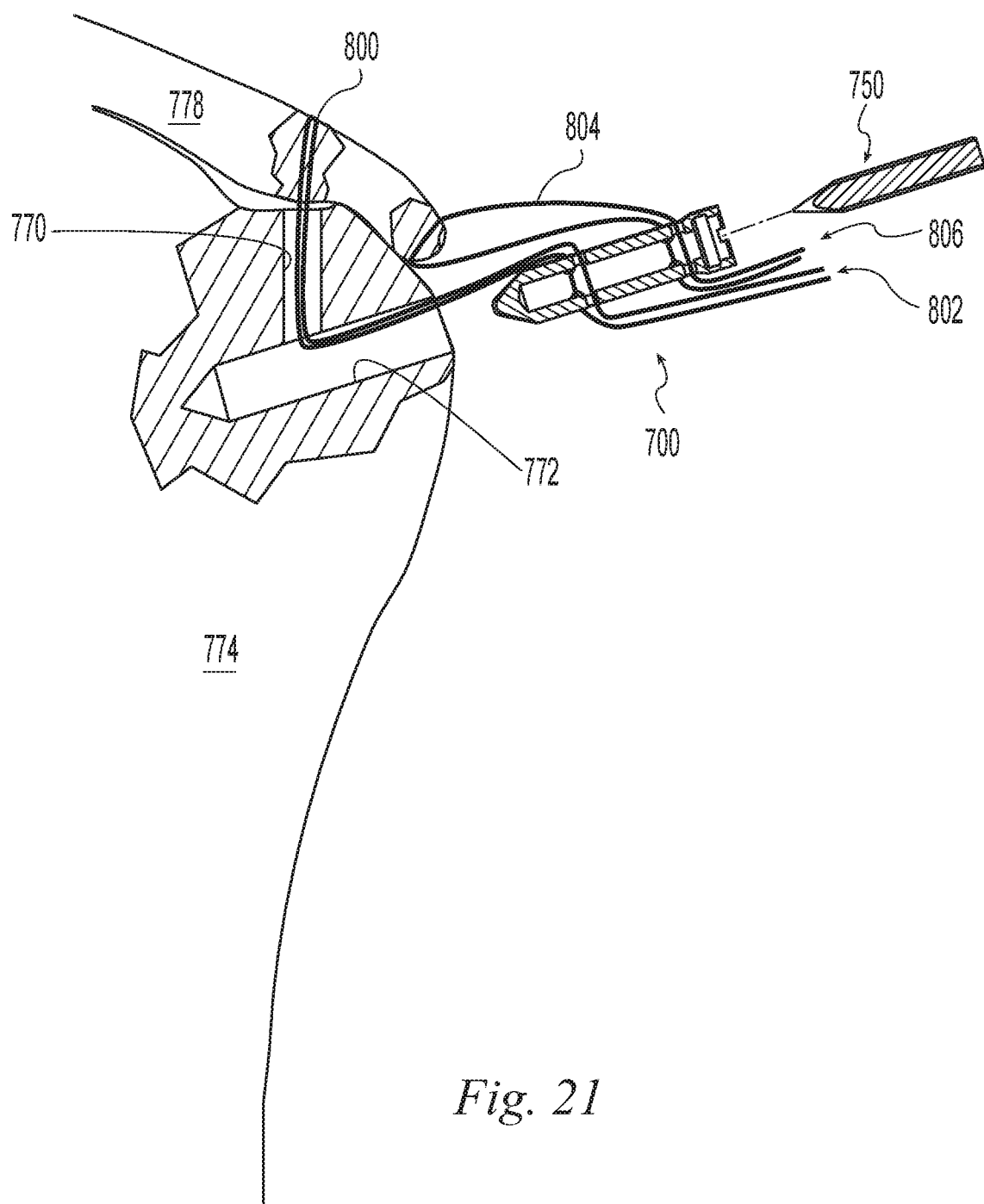
FIG. 21 is a partial side sectional view of the implant of FIG. 10 in use in an alternative method.

FIG. 21 illustrates an alternative method of using the implant 700 in which separate suture strands are passed through separate portions of a soft tissue and the loose ends of each strand are secured using the distal and proximal pairs of apertures respectively. A first suture strand 800 is attached to the rotator cuff 778 such as by way of a mattress stitch or other suitable stitch. The ends 802 of the first suture strand 800 have been passed through the distal apertures 710, 712 of the implant body 700. A second suture strand 804 is attached to the rotator cuff 778 such as by way of a mattress stitch or other suitable stitch. The ends 806 of the second suture strand 804 have been passed through the proximal apertures 714, 716 of the implant body 700. The implant body 700 is inserted into the bone tunnel 772 and the sutures tensioned and secured as describe in the previous illustrative example.

The foregoing examples have illustrated various embodiments of devices and methods useful to attach an elongated strand to a bone by forming a tunnel through the bone, passing the strand through the bone, and then capturing both ends of the strand with a single implant. The embodiments have been illustrated in use to repair a rotator cuff of a shoulder joint but it will be understood that the devices and methods are applicable at other surgical sites to attach other implant and tissues to bone. For example, the devices and methods may be used to attach sutures, tendons, ligaments, cables, implant anchor portions, and/or other objects to bone at surgical locations throughout a patient's body. The devices and methods have been shown in use with first and second transverse, linear, intersecting bone tunnels. However, the devices may be used with single linear tunnels through a bone, curved tunnels, three or more intersecting bone tunnels, and/or other bone tunnel configurations in which it is desired to lock with a single device multiple suture ends.

In the illustrative examples, anchors have been shown securing suture portions at various locations of the anchor. For example, some of the examples have described or depicted fixation at a proximal portion of the anchor and/or at a distal portion of the anchor. The proximal and distal portions of the anchor may refer to distinct proximal and distal ends of the anchor. The proximal and distal portions may refer to relative regions of the anchor such as the proximal one half and distal one half of the anchor, the proximal one third and distal two thirds of the anchor, the proximal two thirds and distal one third or the anchor, or some other fractional part referring to distinct relative zones.

The different illustrative examples have been shown with various forms of bone fixation including threads and annular ridges of varying size and shape. These different forms of fixation may be interchanged within the scope of the invention. For example, where ridges are shown, threads may be substituted and where threads are shown, ridges may be substituted. Any other form of fixation known in the art may also be substituted including but not limited to a smooth press fit.

Some of the illustrative examples have included a plunger receivable within an implant body to lock a suture portion relative to the implant body. In these illustrative examples, the plunger has been shown as engaging the implant body for axial translation by threading, ratcheting, or smooth press fitting into the implant body. These engagement arrangements may be interchanged among the different plunger embodiments. Furthermore, other features for retaining the plunger within the implant body may be incorporated on the plunger and/or within the implant body including ridges, grooves, bumps, surface textures, and/or other retaining features. Furthermore, while the illustrative examples have depicted plungers that are moveable from a proximal position to a distal position in which the suture portion is secured, the plunger may also be moveable from a distal position to a proximal position in which the suture portion is secured. For example, a plunger may be disposed in the implant body distal to a transverse opening and be pulled proximally to secure a suture in the transverse opening.

What is claimed is:

1. A method of attaching a soft tissue to bone, the method comprising:
    forming a bone tunnel through the bone, the bone tunnel having at least first and second spaced apart openings at a surface of the bone;
    inserting a knotless suture anchor into a portion of the bone tunnel such that the knotless suture anchor is fully contained within the bone tunnel, the knotless suture anchor having a proximal end, a distal end and a longitudinal axis extending from the proximal end to the distal end;
    engaging the knotless suture anchor with a suture having a first end and a second end and a mid-portion in between the first and second ends, to form a suture construct securing the soft tissue to the bone wherein the suture construct extends from the knotless suture anchor to the soft tissue and from the soft tissue to the knotless suture anchor, the suture construct passing only once through each of the first opening and the second opening; and
    moving a locking mechanism within the knotless suture anchor to lock the first end and the second end to the knotless suture anchor, and wherein the suture is not routed through the locking member.

2. The method of claim 1 wherein engaging the knotless suture anchor with the suture comprises engaging the knotless suture anchor with the suture to form a loop of suture with first and second suture ends secured by the knotless suture anchor.

3. The method of claim 1 wherein engaging the knotless suture anchor with the suture comprises engaging the knotless suture anchor with a plurality of discrete sutures.

4. The method of claim 1 further comprising:
    passing the suture through the soft tissue prior to engaging the knotless suture anchor with the suture to form the suture construct.

5. The method of claim 4 wherein the suture is positioned with a first suture portion on a first side of the soft tissue and a second suture portion on a second side of the soft tissue, the first suture portion extending from the soft tissue to the knotless suture anchor along a first path through the bone tunnel and the second suture portion extending from the soft tissue to the knotless suture anchor along a second path outside of the bone.

6. The method of claim 5 wherein at least one of the first and second suture portions extends through a portion of the knotless suture anchor and at least one of the first and second suture portions extends along a portion of the outside of the knotless suture anchor.

7. The method of claim 1 wherein moving the locking mechanism locks both the first and second suture ends relative to the knotless suture anchor.

8. The method of claim 1 wherein the knotless suture anchor includes a longitudinal passage extending into an anchor body from the proximal end, and wherein moving the locking mechanism further comprises:
    advancing the locking mechanism in the longitudinal passage.

9. The method of claim 8 wherein the locking mechanism is dimensioned and configured to urge at least one of the first and second suture portions toward an inner wall of the longitudinal passage.

10. The method of claim 1 further comprising:
    after engaging the knotless suture anchor, tensioning the suture.

11. The method of claim 10 further comprising:
    after tensioning the suture, provisionally securing the suture with the knotless suture anchor such that tension on the suture is temporarily maintained; and
    evaluating the suture construct.

12. The method of claim 11 further comprising:
    after evaluating the suture construct, adjusting the suture.

13. The method of claim 1 wherein forming the bone tunnel through the bone comprises forming a bone tunnel through a proximal humeral bone adjacent to a rotator cuff.

14. The method of claim 1 wherein the bone tunnel is formed through the bone as a single continuous path from a first opening on a surface of the bone to a second opening on a surface of the bone.

15. The method of claim 1 wherein the bone tunnel is formed through the bone by first and second intersecting bores into the bone.

16. The method of claim 1 wherein the suture extends from the soft tissue to the first opening, through the first opening to the knotless suture anchor, and the suture extends from the soft tissue outside of the bone tunnel to the second opening, through the second opening to the knotless suture anchor.

17. The method of claim 1, wherein:
moving the locking mechanism within the knotless suture anchor to lock the first end and the second end to the knotless suture anchor comprises:
  locking the first end closer to the proximal end than the distal end; and
  locking the second end closer to the distal end than the proximal end; and
after moving the locking mechanism, the mid-portion extends outside the knotless suture anchor from the proximal end to the distal end.

18. A method of making a transosseous repair of a rotator cuff adjacent a shoulder joint, the method comprising:
forming a bone tunnel through a humeral bone, the bone tunnel having at least first and second spaced apart openings at a surface of the humeral bone;
forming a suture construct securing a portion of the rotator cuff to the humeral bone, without tying any knots,
wherein:
  the suture construct comprises a knotless suture anchor residing entirely within the bone tunnel, the knotless suture anchor having a one-piece anchor body;
  the suture construct extends from the knotless suture anchor to the rotator cuff and from the rotator cuff to the knotless suture anchor, the suture construct passing only once through each of the first opening and the second opening; and
  forming the suture construct further comprises moving a locking mechanism in the knotless suture anchor to secure the suture such that when the suture is secured, the suture has not been passed through the locking mechanism.

19. A method of attaching a soft tissue to a bone, the method comprising:
forming a bone tunnel through the bone, the bone tunnel having at least first and second spaced apart openings at a surface of the bone;
engaging a knotless suture anchor with a suture to form a suture construct securing the soft tissue to the bone by passing the suture through at least one pair of apertures on a longitudinal side of the anchor, the suture construct extending from the knotless suture anchor to the soft tissue and from the soft tissue to the knotless suture anchor, the suture construct passing only once through each of the first opening and the second opening; and
with the suture anchor residing entirely within the bone tunnel, longitudinally translating a locking member within the knotless suture anchor, to lock the suture relative to the knotless suture anchor, and wherein the suture is not routed through the locking member.

20. The method of claim 19 wherein the knotless suture anchor has a longitudinal passageway into which the locking member is translated longitudinally.

* * * * *